United States Patent [19]

Connor et al.

[11] Patent Number: 4,703,053
[45] Date of Patent: Oct. 27, 1987

[54] BENZOTHIOPHENES AND BENZOFURANS AND ANTIALLERGIC USE THEREOF

[75] Inventors: David T. Connor; Wiaczeslaw A. Cetenko; Paul C. Unangst, all of Ann Arbor, Mich.; Elizabeth A. Johnson, Corte Madera, Calif.

[73] Assignee: Warner-Lambert Company, Morris Plains, N.J.

[21] Appl. No.: 790,664

[22] Filed: Oct. 28, 1985

[51] Int. Cl.⁴ .................. C07D 405/04; C07D 405/12; C07D 409/04; A61K 31/41
[52] U.S. Cl. .................................... 514/382; 548/252; 548/253; 548/254
[58] Field of Search ....................... 548/252, 254, 253; 514/382, 381

[56] References Cited

U.S. PATENT DOCUMENTS

| | | | |
|---|---|---|---|
| 3,452,039 | 6/1969 | Buchanan et al. | 548/252 |
| 4,316,904 | 2/1982 | Brown et al. | 548/254 |
| 4,621,091 | 11/1986 | Tischler et al. | 514/337 |

FOREIGN PATENT DOCUMENTS

| | | |
|---|---|---|
| 85302275.4 | 4/1985 | European Pat. Off. . |
| 0146243 | 6/1985 | European Pat. Off. . |

OTHER PUBLICATIONS

B. Samuelsson, "Leukotrienes: Mediators of Immediate Hypersensitivity Reactions and Inflamation," Science, vol. 220, p. 568 (1983).
P. J. Piper, "Leukatrienes:" *Trends in Pharmacological Sciences,* pp. 75 & 77 (1983).
J. L. Romson, et al; "Reduction of the Extent of Ischemic Myocardial Injury by Neutropil Depletion in the Dog," Circulation, vol. 67, p. 1016 (1983).

*Primary Examiner*—Robert T. Bond
*Assistant Examiner*—D. B. Springer
*Attorney, Agent, or Firm*—Joan Thierstein

[57] ABSTRACT

Novel benzothiophene and benzofuran derivatives having antiallergic activity are described as well as a method of manufacture, pharmaceutical compositions, and methods of use therefor. The disclosure describes the use of derivatives for prevention of the release of mediators including histamine and leukotrienes from basophils and mast cells, and prevent respiratory burst in neutrophils providing activity useful in cardiovascular disorders as well as in antiinflammatory, psoriasis, and antimigraine treatment.

51 Claims, No Drawings

BENZOTHIOPHENES AND BENZOFURANS AND ANTIALLERGIC USE THEREOF

This application is a continuation-in-part of U.S. Ser. No. 680,108 filed Dec. 10, 1984, now abandoned.

BACKGROUND OF THE INVENTION

The present invention provides novel benzothiophene and benzofuran compounds, novel methods for synthesis thereof, selected novel intermediates, pharmaceutical compositions, and uses of the novel compounds particularly as antiallergic agents. Additionally, the compounds prevent the release of mediators including histamine and leukotrienes from basophils and mast cells, and prevent respiratory burst in neutophils providing activity useful in cardiovascular disorders as well as in antiinflammatory, psoriasis, and antimigraine treatment. These compounds act as inhibitors of cell activation. See B. Samuelsson, "Leukotrienes' Mediators of Immediate Hypersensitivity Reactions and Inflammation," *Science*, Vol. 220, p 568 (1983), P. J. Piper, "Leukotrienes," *Trends in Pharmacological Sciences*, pp 75 & 77 (1983), and J. L. Romson, et al; "Reduction of the Extent of Ischemic Myocardial Injury by Neutrophil Depletion in the Dog," *Circulation*, Vol. 67, p 1016 (1983)

European patent application No. (EP) 0146243 discloses a series of benzofuran and benzothiophene compounds. However, the benzothiophenes of the present invention are not included in EP No. 014623 and the benzofurans of the present invention cannot be made by the processes disclosed in EP No. 0146243.

European patent publication No. 69,521 discloses benzothiophene derivatives. However, the novel compounds of the present invention include differences, for example, having tetrazole and carboxamide substitutents, from the compounds in EP No. 069,521 not suggested by its disclosure. Additionally, U.S. Pat. No. 3,452,039 discloses benzothiophene derivatives, however, the substitutents of the present compounds are not shown.

Furthermore, the antiallergic utility now found for novel compounds of the present invention is not within the teachings for the benzothiophene compounds disclosed by either the EP No. 69,521 reference or the U.S. Pat. No. 3,452,039.

SUMMARY OF THE INVENTION

The present invention is a compound of Formula (I),

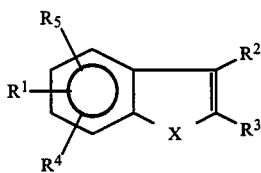

I wherein (1) $R^1$, $R^4$, and $R^5$ are independently H, alkyl of from one to twelve carbons, inclusive, alkoxy of from one to twelve carbons, inclusive, hydroxy, aryl, $R^1$ taken twice having each on adjacent carbons such that the two $R^1$s together are methylenedioxy, nitro, amino, substituted amino, mercapto, alkylthio of from one to four carbons inclusive, alkylsulfinyl of from one to four carbons, inclusive, alkylsulfonyl of from one to four carbons, inclusive, arylthio, arylsulfinyl, arylsulfonyl, or halogen; (2) $R^2$ is H, alkyl of from one to twelve carbons, inclusive, alkoxy of from one to twelve carbons inclusive, arylmethoxy, amino, substituted amino, mercapto, alkylthio of from one to four carbons, inclusive, alkylsulfinyl of from one to four carbons, inclusive, alkylsulfonyl of from one to four carbons, inclusive, arylthio, arylsulfinyl, or arylsulfonyl; and (3) $R^3$ is A or B with the proviso that when $R^3$ is B then $R^2$ cannot be H or alkyl of from one to twelve carbons, inclusive; (4) X is oxygen or S(0)q wherein q is zero, one, or two; and pharmaceutically acceptable salts thereof.

Further, the present invention includes a process for the preparation of a compound of Formula I wherein $R^1$, $R^4$, $R^5$, $R^2$, and $R^3$ are as defined above, which comprises treating a compound having the Formula III, wherein $R^1$ and $R^2$ are as defined above to obtain the compound of Formula I as shown in Scheme I.

The process of Scheme II which comprises treating the compound of Formula III or III[3] wherein $R^6$ is each the same or different and is hydrogen, alkyl of from one to six carbons, or a protecting group with the proviso that not both of $R^6$ are hydrogen; with the compound of Formula II₁; in the presence of a coupling agent to obtain the compound of Formula I₁, wherein $R_3$ of Formula I is the moiety shown by A.

Suitable coupling reagents for the conversion of the compounds of the Formula III or of the Formula III[3] are 1,1-carbonylbis(1 H-imidazole), 1,3-dicyclo hexylcarbodiimide, 1-ethoxycarbonyl-2-ethoxy-1,2-dihydroquinoline (EEDQ) and the like. The N($R^6$)₂ group in III[3] is subsequently treated to remove the protecting group, if necessary.

A compound of Formula III is known or can readily be prepared from compounds known in the literature. For example, compounds of Formula III wherein $R^2$ is an amino or a substituted amino may be prepared by methods analogous to those described by James R. Beck, *J. Org. Chem.*, Vol. 37, No. 21, pp 3224–6 (1972). Beck described compounds in which X is sulfur and the substituent $R^2$ is an amino. Substituted amino groups can be prepared from the amino compounds by standard methods. Compounds of Formula III wherein X is oxygen and $R^2$ is amino or substituted amino may be prepared by methods shown in Scheme IV using conditions analogous to those known in the literature. Particularly, selected compounds having X as oxygen in the Formula III[3], III[4], and III[5] of Scheme IV are found in the literature, for example, K. Gewand and H-J. Jansch, *J. Prakt. Chem.;* 315, 779 (1973), F. A. Trofimov, et al, *Chem. Het. Comp.*, 11, 1129 (1975); and S. B. Mahajan and Y. S. Agasimundin, *J. Ind. Chem. Soc.*, 54, 965 (1977). Scheme IV shows the use of an acetyl protecting group. Other known protecting groups may be used as noted hereinafter. Substituents in the $R^1$ position of the compound III (not described by Beck) may be obtained by other known methods.

For example, for compound I where X is oxygen, $R^2$ is alkoxy or arylmethoxy, and $R^3$ is COOH or A; preparation of precursors is shown in Scheme V. Suitable alkylation reagents for the conversion of III[2] to III[1] are alkyl halides, alkylsulfonates, O-alkyl-N,N'-dialkylisoureas, and the like. Particularly, compounds of the Formula III[2], III[1], and III where X is oxygen are described by J. D. Brewer, et al, in *Aust. J. Chem.*, 24, 1883(1971), by E. C. Schroeder, et al, in *J. Org. Chem.*, 27, 586(1962), and By K. v. Auwers, in *Chem. Ber.*, 61, 408(1928).

Compounds of Formula III wherein $R^2$ is a mercapto or alkyl or aryl mercapto within the present invention may be made by procedures analogous to those shown to prepare the mercapto containing compounds in the following Examples 1A-E, 2A-E, or 6A-E, or other known methods. Likewise, compounds of Formula III wherein $R^2$ is alkylsulfinyl and arylsulfinyl or alkysulfonyl and arylsulfonyl described herein can be prepared by known methods adapted to the preparation of such a compound from a mercapto by alkylation or arylation and then oxidation.

The process which comprises treating the compound of Formula III to obtain the compound of Formula $I_2$ wherein $R^3$ of Formula I is the moiety shown by B is one in which the compound of Formula III is treated by methods analogous to those known in the art to give a compound of Formula IV, wherein $R^1$ and $R^2$ are as defined above, e.g., see T. Kamijo, et al, Chem. Pharm. Bull., 32 (7) 12560–4 (1984), and see also for compounds of Formula IV where X is oxygen M. Pesson and Joannic, British patent No. 1,233,268, issued May 26, 1971, R. Bryant, and D. L. Haslam, J. Chem. Soc., 2361 (1965), and S. S. Sangapure and Y. S. Agasimundin, *Ind. J. Chem.*, 14B, 6886 (1976), and the compound of Formula IV is then treated in a manner analogous to that described by R. D. Buchanan, et al, in U.S. Pat. No. 3,452,039 cited as a reference herein before. See Scheme III.

The antiallergy activity of the compounds having the Formula I of the present invention was determined by the well-known Schultz-Dale procedure, that is described in N. Chand, et al, *Agents and Actions*, 8, 171 (1978) or the Herxheimer in vivo antiallergy test described in H. Herxheimer, J. Physiol. (London) Vol. 117,251 (1952).

By virtue of this antiallergy activity the compounds of Formula I are useful in treating an allergic hypersensitivity reaction (AHR) having broad symptoms. For example, the symptoms may include dermatitis, lacrimation, nasal discharge, coughing, sneezing, nausea, vomiting, diarrhea, difficulty in breathing, pain, inflammation, and in severe cases, anaphylactic shock, circulatory collapse, and even death. The AHR is found in man as well as other animals suffering from bronchial asthma, seasonal pollinosis (e.g., hayfever), allergic rhinitis, urticaria, allergic conjunctivitis, food allergies, and anaphylactoid reactions.

In an AHR an antibody (reagin in man) influences the cell membrane of a mast cell by reacting with an antigen, to initiate reactions within the mast cell which ultimately causes release of mediators (bioactive compounds) such as bradykinin, slow reacting substance of anaphylaxis (SRS-A), histamine, serotonin (5HT), possibly some prostaglandins, or other not now known substances. The mediator is released from the mast cell whereupon it attaches to suitable receptor sites (e.g., on smooth muscle) resulting in AHR attack symptoms. Various methods are used to relieve the symptoms of AHR. It is not known, however, what mechanism is effected for the antiallergic use by the compounds having Formula I of the present inventions.

Pharmaceutical compositions are prepared from compounds of Formula I and salts thereof described as the present invention having inert pharmaceutical carriers. The compositions may be either solid or liquid.

A physician or veterinarian of ordinary skill readily determines a subject who is exhibiting AHR symptoms. Regardless of the route of administration selected, the compounds of the present invention are formulated into pharmaceutically acceptable dosage forms by conventional methods known to the pharmaceutical art.

The compounds can be administered in such oral unit dosage forms such as tablets, capsules, pills, powders, or granules. They also may be administered rectally or vaginally in such forms as suppositories or bougies; they may also be introduced parenterally (e.g., subcutaneously, intravenously, or intramuscularly), using forms known to the pharmaceutical art. They are also introduced directly to an affected area, (e.g., in the form of eye drops or by inhalation). For the treatment of AHR induced conditions such as erythema, the compounds of the present invention may also be administered topically in the form of ointments, creams, gels, or the like. In general, the preferred route of administration is orally.

An effective but nontoxic quantity of the compound is employed in treatment. The ordinarily skilled physician or veterinarian will readily determine and prescribe the effective amount of the anti-AHR agent to prevent or arrest the progress of the condition. In so proceeding, the physician or veterinarian could employ relatively low dosages at first, subsequently increasing the dose until a maximum response is obtained.

Initial dosages of the compounds of the invention having Formula I are ordinarily in the area of 10 mg up to 2 g per day orally, preferably 10 mg to 500 mg per dose orally, given from one to four times daily or as needed. When other forms of administration are employed equivalent doses are administered.

The compounds of this invention can also be administered as pharmacologically acceptable salts such as can be readily prepared with inorganic and organic bases, such as NaOH, KOH, $Mg(OH)_2$, $Ca(OH)_2$, $NH_4OH$, substituted ammonium salts, L-arginine, choline, N-methyl glucamine and the like.

The novel compounds of Formula I are named as derivatives of benzothiophenes or benzofurans by virtue of a sulfur or oxygen containing heterocyclic five-membered ring fused to a phenyl ring. The fused rings are numbered counterclockwise starting with the sulfur or oxygen atom at the one position as shown in the ring system of Formula I'.

Certain compounds within the scope of Formula I as defined above are preferred. Among the preferred compounds of Formula I are those wherein $R^3$ is the substituent A, i.e., carboxamidotetrazole. Also among the preferred compounds are those wherein $R^1$ is methoxy, particularly in the five or six positions. More preferred are the following compounds: (1) 5-methoxy-3-(1-methylethoxy)-N-1H-tetrazol-5-yl-benzo(b)thiophene-2-carboxamide, (2) 3,5-dimethoxy-N-1H-tetrazol-5-yl-benzo[b]thiophene-2-carboxamide, (3) 6-methoxy-3-(1-methylethoxy)-N-1H-tetrazol-5-yl-benzo [b]thiophene-2-carboxamide, (4) 3-(1-methylethoxy)-N-1H-tetrazol-5-yl-benzothiophene-2-carboxamide, (5) 5-methoxy3-[(1-methylethyl)-thio]-N-1H-tetrazol-5-yl-benzo [b]-thiophene-2-carboxamide, and (6) 6-methoxy-3-(phenylmethoxy)-N-1H-tetrazol-5-yl-2benzofurancarboxamide.

Of the above, the most preferred compounds are (1), (3), and (5).

Alkyl of from one to four carbons, inclusive, is methyl, ethyl, propyl, butyl, or isomeric forms therof.

Alkyl of from one to twelve carbons, inclusive is methyl, ethyl, propyl, butyl, pentyl, hexyl, heptyl octyl, nonyl, etc, and includes isomeric forms of the alkyl of from one to six carbons, inclusive. Alkyl of from one to six carbons, inclusive, are preferred.

Alkoxy of from one to twelve carbons, inclusive, is methoxy, ethoxy, propoxy, butoxy, etc, and includes isomeric forms of alkoxy of from one to six carbons, inclusive. Alkoxy of from one to six carbons, inclusive are preferred.

Substituted amino is mono- or di- alkylamino wherein the alkyl may be the same or different from one to six carbons when taken alone or together.

Halogen is chloro, bromo, fluoro, iodo, or trifluoromethyl.

Aryl is phenyl or substituted phenyl having one or two substitutions, such as halogen, alkyl of from one to six carbons, inclusive, alkoxy of from one to six carbons, inclusive, hydroxy, nitro, amino, substituted amino, and the like.

Generally, the compounds having the Formula I, wherein $R^1$ and $R^2$ are as defined above, and $R^3$ is the substituent A are prepared by treating the compound of Formula III wherein $R^1$ and $R^2$ are as defined by one of two methods.

The first method shown as Scheme II which is preferred treats the compound III with 5-aminotetrazole in the presence of a coupling agent and triethylamine. About 20% excess of the 5-aminotetrazole, the coupling agent, and the triethylamine compared to one equivalent of the compound III is preferred. Coupling agents may include 1,1'-carbonylbis(1H-imidazole) dicyclohexylcarbodiimide, 1,3-diisopropylcarbodiimide, and the like. Solvents for the method may include one or more of tetrahydrofuran, dimethylformamide, acetonitrile, and the like, but preferably the solvent is acetonitrile. The mixture is refluxed for from about 4 to 24 hours.

The second method also generally shown as Scheme II is accomplished by reacting the compound of Formula III, and 5-aminotetrazole in the presence of the coupling agent, all in equivalent amounts in a solvent such as tetrahydrofuran; that is preferred, dioxane, dimethylformamide, dimethylsulfoxide, and the like.

Generally, the coupling reaction shown in Scheme II includes variations known to one of skill in the art.

The above compound of Formula $I_1$ is separated and purified by conventional methods or may be used in crude form.

Under certain circumstances it is necessary to protect either the N or O of intermediates in the above noted process with suitable protecting groups which are known. Introduction and removal of such suitable oxygen and nitrogen protecting groups are well known in the art of organic chemistry; see for example, (1) "Protective Groups in Organic Chemistry," J. F. W. McOmie, ed., (New York, 1973), pp 43ff, 95ff; (2) J. F. W. McOmie, *Advances in Organic Chemistry*, Vol. 3, 191–281 (1963); (3) R. A. Borssonas, *Advances in Organic Chemistry*, Vol. 3, 159–190 (1963); and (4) J. F. W. McOmie, *Chem. & Ind.*, 603 (1979).

Examples of suitable oxygen protecting groups are benzyl, t-butyldimethylsilyl, methyl, isopropyl, ethyl, tertiary butyl, ethoxyethyl, and the like. Protection of an N-H containing moiety is necessary for some of the processes described herein for the preparation of compounds of this invention. Suitable nitrogen protecting groups are benzyl, triphenylemethyl, trialkylsilyl, trichloroethylcarbamate, trichloroethoxycarbonyl, vinyloxycarbamate, and the like.

Under certain circumstances it is necessary to protect two different oxygens with dissimilar protecting groups such that one can be selectively removed while leaving the other in place. The benzyl and t-butyldimethylsilyl groups are used in this way; either is removable in the presence of the other, benzyl being removed by catalytic hydrogenolysis, and t-butyldimethylsilyl being removed by reaction with, for example, tetra-n-butylammonium fluoride.

In the process described herein for the preparation of compounds of this invention the requirements for protective groups are generally well recognized by one skilled in the art of organic chemistry, and accordingly the use of appropriate protecting groups is necessarily implied by the processes of the charts herein, although not expressly illustrated.

The products of the reactions described herein are isolated by conventional means such as extraction, distillation, chromatography, and the like.

Variations in the above described processes may be the present invention including appropriate intermediate steps to convert mercapto to —$SO_2$-alkyl substituents, to convert a nitrile to carboxylic acid substituent, or protection of O and N containing substituents by suitable groups as described above.

The salts of compounds of Formula I described above are prepared by reacting the appropriate base with a stoichometric equivalent of the acid thiophene or benzofuran compounds of Formula I to obtain pharmacologically acceptable salts thereof.

The compounds of this invention may also exist in hydrated or solvated forms.

DESCRIPTION OF THE PREFERRED EMBODIMENTS

The process of this invention is further elaborated by the representative examples as follows.

EXAMPLE 1 (A)

Methyl-4-methoxysalicylate (Graebe and Martz, Ann. 340, 215 (1909), bp 235°–240° C.)

A mixture of 4-methoxysalicylic acid (Aldrich) (178.1 g, 1.06 mmole) sodium bicarbonate (89 g, 1.06 mole), and dimethyl sulfate (133.6 g, 1.06 mole) in acetone (2 l) is refluxed with stirring under nitrogen for 20 hours. The mixture is cooled, filtered, and the acetone is removed under reduced pressure to yield an oily residue. The residue is taken up in ether (1.8 l) and toluene (0.50 l). The extracts are washed with sodium bicarbonate solution, water, dried over sodium sulfate, and concentrated to give a syrup (190.9 g). Recrystallization from hexane gives 172.7 g (89.5%) of analytically pure solid, mp 49°–50° C.

EXAMPLE 1 (B)

Benzoic acid, 4-methoxy-2-[(dimethylamino)thioxomethoxy]-methyl ester

To a solution of methyl 4-methoxysalicylate (171.7 g, 0.94 mole) and 1,4-diazabicyclo [2.2.2]octane (233.9 g, 2.02 mole) in sieve dried dimethylformamide (1 l) is added rapidly dimethylthiocarbamoyl chloride (250 g, 2.02 mole) with stirring under nitrogen. The resulting mixture is stirred at room temperature for 1.75 hours, then at 50° for 18 hours. The mixture is cooled, poured into ice water (~3 l) and extracted twice with toluene (2 l, 1.5 l). The combined toluene extracts are washed successively with dilute hydrochloric acid, water, cold sodium bicarbonate solution, and water. The extract is dried over sodium sulfate. Removal of the solvent under reduced pressure afforded crude product, which is recrystallized twice from methanol to give 192.6 g (76%) of analytically pure product, mp 126°-7° C.

EXAMPLE 1 (C)

Benzoic acid, 4-methoxy-2[(dimethylamino)carbonyl)thio]- methyl ester

A solution of benzoic acid, 4-methoxy-2[(dimethylamino)thioxomethoxy]methyl ester (188 g) in diphenyl ether (1140 g) is heated at 237°–255° C. under an atmosphere of nitrogen for 14 hours. After cooling to room temperature the contents of the flask are poured into hexane (~2.5 l) and stirred for one-half hour at ~10° C. The crystalline precipitate formed is collected and recrystallized from methanol to give 139.1 g (74%) of analytically pure product, mp 74°-5° C.

EXAMPLE 1(D)

4-Methoxy-thiosalicylic acid (Leon Katz et al, U.S. Pat. No. 2,767,173 (1956), CA51, P6704b (1957), cites mp 240° (prepared by diazotization of 4-methoxyanthranilic acid, etc)

A mixture of benzoic acid, 4-methoxy-2[(dimethylamino)carbonyl)thio]methyl ester (122.8 g, 0.46 mole) sodium hydroxide (47.4 g, 1.15 mole), methanol (940 ml), and water (470 ml) is refluxed with stirring under nitrogen for 13 hours. Most of the methanol is removed at 50° C. under water aspirator pressure. The solution is cooled, diluted with ice water to ~3 l volume and carefully acidified with aqueous hydrochloric acid, while the temperature is maintained below 15° C. The solid is collected, washed with water, and dried to give 83.2 g (98.5%) of analytically pure product, mp 237° C.

EXAMPLE 1 (E)

Methyl-4-methoxythiosalicylate (Leon Katz, et al, J. Org. Chem. 18, 1380-1402 (1953) gives yield 88% and general method for the esterification (acid+CH₃OH+HCl (g)→ester), but no other data.

A mixture of 4-methoxythiosalicylic acid (83.15 g, 0.45 mole), methanol (2 l), and concentrated sulfuric acid (92 ml) is refluxed with stirring under nitrogen for 17.75 hours. Most of the methanol is removed at 40° under water aspirator pressure. The reaction mixture is cooled, poured into ice water, and extracted with ether. The ethereal extracts are washed with cold sodium bicarbonate solution, water, and dried over sodium sulfate. After evaporation of the solvent under vacuum the crude oil (82.8 g) is distilled under high vacuum to give 77.3 g (86.9%) of analytically pure solid, mp 38°-9° C.

EXAMPLE 1 (F)

Benzo[b]thiophene-2-carboxylic acid, 3-hydroxy-6-methoxy-, methyl ester

A mixture of methyl 4-methoxythiosalicylate (76.4 g, 0.39 mole) and potassium-t-butoxide (45 g, 10.4 mole) in dimethyl sulfoxide (500 ml) is held at 20°–30° while methyl chloroacetate (41.8 g, 0.39 mole) is added dropwise over 15 minutes with stirring under nitrogen. Stirring is continued at room temperature for ten minutes, then the mixture is heated on a steam bath for 30 minutes. The solution is cooled to 50° and an additional portion of potassium t-butoxide (45 g) is added. The mixture is heated on a steam bath for 4.5 hours and left standing overnight at room temperature. The mixture is then poured into ice water (~4 l) and carefully acidified with dilute hydrochloric acid. The precipitate is filtered off, washed with water, and dried to give 100 g of a solid, mp 122°-3°. Crystallization from acetone- (decolorized with charcoal) -methanol, then from methylene chloride -methanol yields 75 g (81.8%) of analytically pure product, mp 124°-5° C.

EXAMPLE 1 (G)

Benzo[b]thiophene-2-carboxylic acid, 6-methoxy-3-(1-methylethoxy)-

(A) A mixture of benzo[b]thiophene-2-carboxylic acid, 3-hydroxy-6-methoxy, methyl ester (23.8 g, 0.1 mole) and N,N',O-triisopropyl, pseudourea (Erich Schmidt and Fritz Moosmüller, Ann. 597, 235–40 (1955)) (74.5 g, 0.4 mole) in acetonitrile (400 ml) is refluxed with stirring under nitrogen for 23 hours and then cooled. The solid (N,N'-diisopropylurea) is filtered off. The solvent and volatiles are removed under vacuum, and then under high vacuum. The residue is dissolved in ether, filtered, and the solid is discarded. After evaporation of the solvent under vacuum the residue is dissolved in methylene chloride and filtered on a silica gel (220 g) column to give 27.4 g (97.8%) of benzo[b]thiophene-2-carboxylic acid-6-methoxy-3(1-methylethoxy), methyl ester, which is used directly in the next stage.

(B) A mixture of crude ester from the previous stage (27.4 g), potassium hydroxide (11.8 g), and methanol (300 ml) is refluxed with stirring under nitrogen for 2.75 hours. Most of the methanol is then removed under reduced pressure at 45°. The residue is dissolved in water (~750 ml) and decolorized with activated charcoal. After cooling the solution is carefully acidified with dilute hydrochloric acid, while the temperature is maintained below 15°. The crystalline precipitate is filtered, washed with water, and dried to give 24.09 g of a solid, mp 159° (dec). Recrystallization from acetonitrile gives 22.85 g (85.8%) of analytically pure product, mp 159°–160° C. (dec).

EXAMPLE 1(H)

Benzo[b]thiophene-2-carboxamide, 6-methoxy-3-(1-methylethoxy)-N-1H-tetrazol-5-yl A mixture of benzo[b]thiophene-2-carboxylic acid-6-methoxy-3(1-methylethoxy) (10.41 g, 0.039 mole) and 1,1'-carbonyldiimidazole (7.61 g, 0.047 mole) in acetonitrile (200 ml) is refluxed with stirring under nitrogen for 80 minutes. A solution of 5-aminotetrazole (3.99 g, 0.047 mole) and triethylamine (4.75 g, 0.047 mole) in acetonitrile (100 ml) is added dropwise. The mixture is heated at reflux for 21.5 hours, then most of the acetonitrile is removed under water aspirator pressure at 40°. The residue is treated with cold water (~700 ml) then acidified with acetic acid (14.5 g). The resulting solid is separated by filtration, washed with water, then with ether, and dried to give 12.1 g of a solid. Recrystallization from methanol gives 11.06 g (84.9%) of analytically pure product, mp 237°-9° C. (dec).

EXAMPLE 2(A)

Methyl-5-methoxysalicylate

Treatment of 5-methoxysalicylic acid (Aldrich) (151.6 g, 0.9 mole) with sodium bicarbonate (75.74 g, 0.9 mole) and dimethyl sulfate (113.7 g, 0.9 mole) in acetone (1.5 1) by the method of Example 1(A), gives 149 g (90.7%) of analytically pure oil, bp °/0.05 mm.

EXAMPLE 2(B)

Benzoic acid, 5-methoxy-2-(dimethylamino)thioxomethoxy)- methyl ester

Treatment of methyl-5-methoxysalicylate (149 g, 0.82 mole) and 1,4-diazabicyclo[2.2.2] octane (257.3 g, 2.22 mole) in dimethylformamide (1 1) with dimethylthiocarbamoyl chloride (275 g, 2.22 mole) by the method of Example 1(B) gave the product. Two recrystalizations from methanol gives 157.9 g (71.7%) of analytically pure product, mp 102°-3° C.

EXAMPLE 2(C)

Benzoic acid, 5-methoxy-2[(dimethylamino)carbonyl)thio]- methyl ester

Treatment of benzoic acid, 5-methoxy-2-[(dimethylamino)thioxomethoxy]-methyl ester (150 g) in diphenyl ether (1416 g) by the method of Example 1(C) gave the product. Recrystallization from methylene chloridehexane gives 92.9 g (61.9%) of analytically pure product, mp 70°-2° C.

EXAMPLE 2(D)

5-Methoxythiosalicylic acid (F. Sauter and P. Stütz, Monatsh. Chemie, 98, 1962 (1967), mp 300°-1° C. (170-3); O. Francis Bennet et al, Organic Preparation and Procedures Int. 6(6)287-293 (1974), mp 175°-6° C. Prepared by different methods.)

Treatment of benzoic acid, 5-methoxy-2-[(dimethylamino)carbonyl)thio)]methyl ester (90.7 g, 0.34 mole) with sodium hydroxide (35 g), methanol (700 ml), and water (350 ml) by the method of Example 1(D) gives 60.9 g (97.6%) of pure product, mp 170°-2° C.

EXAMPLE 2(E)

Benzo[b]thiophene-2-carboxylic acid, 3-hydroxy-5-methoxy-methyl ester (A) A mixture of methyl-5-methoxythiosalicylate (O. Francis Bennet et al, Organic Preparations and Procedures Int. 6(6), 287-293 (1974) cites b.p. 105-6/0.3 mm) (51.12 g, 0.26 mole) and potassium-t-butoxide (29.7 g, 0.27 mole) in dimethyl sulfoxide (250 ml) is held at 10°-30° while methyl chloroacetate (28 g, 0.26 mole) is added dropwise with stirring under nitrogen. After the introduction is terminated, stirring is continued at room temperature for ten minutes. The resulting mixture is heated on a steam bath for 1.75 hours. After cooling, the reaction mixture is added to ice water (~1.7 1) and extracted with ether (2 1, 1 1). The combined extracts are washed with water and dried over sodium sulfate. The solvent is removed under reduced pressure to give 67.5 g of a semisolid residue, which is recrystallized twice from methanol to give 9.4 g (15.3%) of the product, mp 133°-4° C. The filtrate is concentrated to give 41.3 g (in two crops) of Methyl 2-(carbomethoxymethylthio)-5-methoxybenzoate, mp 55°-7° C., which is used directly in the next stage.

(B) To a solution of sodium methoxide (from 3.45 g, 0.15 mole sodium metal and 400 ml methanol) is added rapidly diester (41 g, 0.15 mole) (from the previous stage) with stirring. Stirring is continued at room temperature for 20 minutes, and then the mixture is refluxed on a steam bath for four hours. After cooling to room temperature, the reaction mixture is diluted with water (~4 1) and filtered through super cell Hyflo and Darco G-60 mat. The solution obtained is cooled, and carefully acidified with dilute hydrochloric acid. Filtration of the resulting solid (27.3 g) and recrystallization from methylene chloride-methanol gives 26.8 g (74%) of analytically pure product, mp 133°-134 C., making the combined yield 59%.

EXAMPLE 2(F)

Benzo[b]thiophene-2-carboxylic acid, 5-methoxy-3-(1-methylethoxy)

(A) To a mixture of benzo[b]thiophene-2-carboxylic acid-3-hydroxy-5-methoxy, methyl ester (10 g, 0.042 mole) and 2-bromopropane (11.3 g, 0.091 mole) in dimethyl sulfoxide (150 ml) is added potassium-t-butoxide (5.4 g, 0.048 mole). The mixture is then heated at 100° with stirring under nitrogen for seven hours and left standing over night. The resulting mixture is then poured into ice water and extracted with ether. The organic phase is washed with cold dilute potassium carbonate solution and water, dried over sodium sulfate, and concentrated to 10.36 g of dark oil, namely, benzo[b]thiophene-2-carboxylic acid-5-methoxy-3-(1-methylethoxy)-methyl ester, which is used directly in the next stage.

(B) Mixture of crude ester (10.36 g) from the previous stage, potassium hydroxide (3.8 g) and methanol (100 ml) is treated according to the procedure of Example 1(GB). There is obtained 7.24 g (65%) of the product, mp 133°-4°, which is recrystallized from acetonitrile to give 6.0 g (53.8%) of analytically pure product, mp 133°-4° C.

EXAMPLE 2(G)

(A) Benzo[b]thiophene-2-carboxamide, 5-methoxy-3-(1-methylethoxy)-N-1H-tetrazol-5yl-, comp. with 1H-imidazole (1:1)

A mixture of benzo[b]thiophene-2-carboxylic acid, 5-methoxy-3-(1-methylethoxy) (5.35 g, 0.02 mole) and 1,1'-carbonyldiimidazole (3.26 g, 0.02 mole) in tetrahydrofuran (200 ml) is stirred under nitrogen for two hours. To this solution 5-aminotetrazole (1.71 g, 0.02 mole) is added and the resulting mixture is stirred at room temperature for 17 hours, then is refluxed for two hours. The mixture is filtered and the filtrate is concentrated under reduced pressure to give a solid, which is washed with ether. Recrystallization from methanol gives 2.2 g (27.4%) of analytically pure product, mp 187°-9° C.

(B) Benzo[b]thiophene-2-carboxamide, 5-methoxy-3-(1-methylethoxy)-N-1H-tetrazol-5-yl- A mixture of benzo[b]thiophene-2-carboxylic acid, 5-methoxy-3(1-methylethoxy) (10.41 g, 0.039 mole), 1,1'-carbonyldiimidazole (7.641 g, 0.047 mole) 5-aminotetrazole (3.99 g, 0.047 mole) and triethylamine (4.75 g, 0.047 mole) in acetonitrile (300 ml) is treated according to the procedure in Example 1(H). There is obtained 11.65 g of the product, mp 214°-6° C. (dec). Recrystallization from methanol gives 9.25 g (71%) of analytically pure product, mp 214°-6° C. (dec).

(C) Benzo[b]thiophene-2-carboxamide, 5-methoxy-3-(1-methylethoxy)-N-1H-tetrazol-5-yl-sodium salt To a stirred suspension of benzo[b]thiophene-2-carboxamide, 5-methoxy-3-(1-methylethoxy)-N-1H-tetrazol-5-yl (6.99 g, 0.021 mole) in methanol (500 ml) is added a solution of sodium hydroxide (0.86 g, 0.021 mole) in water (40 ml). The reaction mixture is stirred at room temperature until a clear solution is obtained, then the solvents are removed under water aspirator pressure below 60° C. The residue is taken up in methanol (~150 ml) and ethanol (350 ml) and the solvents are removed. This procedure is repeated twice more, then the residue is dissolved in a minimum volume of methanol and ether is added. The resulting solid is collected, washed with ether, and dried to give 5.3 g (69.7%) of analytically pure product, mp 190°-210° C.

EXAMPLE 3(A)

Benzo[b]thiophene-2-carboxylic acid, 3,5-dimethoxymethyl ester

A mixture of benzo[b]thiophene-2-carboxylic acid, 3-hydroxy-5-methoxy-methyl ester (7.8 g, 0.033 mole), potassium carbonate (4.5 g, 0.033 mole), and dimethyl sulfate (4.7 g, 0.037 mole) in acetone (300 ml) is refluxed with stirring under nitrogen for 15.5 hours. The mixture is cooled, filtered, and acetone is removed at 45° under water aspirator pressure. The residue is treated with water and extracted with ether. The ether extracts are washed with water, dried over sodium sulfate and the solvent is removed to give 7.8 g of a solid, mp 102°-3° C. Recrystallization from methylene chloride-methanol gives 7.47 g (92.5%) of analytically pure product, mp 102°-3° C.

EXAMPLE 3(B)

Benzo[b]thiophene-2-carboxylic acid, 3,5-dimethoxy-

Treatment of benzo[b]thiophene-2-carboxylic acid, 3,5-dimethoxy methyl ester (6.76 g, 0.027 mole) with methanolic potassium hydroxide by the method of Example 1(G), gives 5.55 g (87.3%) of analytically pure product, mp 190° C. (dec) (from methanol).

EXAMPLE 3(C)

Benzo[b]thiophene-2-carboxamide, 3,5-dimethoxy-N-1H-tetrazol-5-yl-

A mixture of benzo[b]thiophene-2-carboxylic acid, 3,5-dimethoxy (4.58 g, 0.019 mole), 1,1'-carbonyl-diimidazole (3.17 g, 0.019 mole) and 5-amino-tetrazole (1.64 g, 0.019 mole) in tetrahydrofuran (250 ml) is treated according to the procedure in Example 2 (G). There is obtained 5.8 g of a solid. Recrystallization from methanol-tetrahydrofuran-acetonitrile gives 2.8 g (47.8%) of analytically pure solid, mp 213°-5° C. (dec).

EXAMPLE 4(A)

Benzo[b]thiophene-2-carboxylic acid, 3-ethoxy-5-methoxy- (A) A mixture of benzo[b]thiophene-2-carboxylic acid, 3-hydroxy-5-methoxy, methyl ester (10 g, 0.042 mole) potassium carbonate (15.8 g, 0.042 mole), and diethyl sulfate (7.32 g, 0.047 mole) in acetone (500 ml) is refluxed with stirring under nitrogen for 24 hours. The acetone is then evaporated. The residue is treated with potassium carbonate (5.8 g), diethyl sulfate (8 g), and dimethyl sulfoxide (150 ml). The mixture is heated on a steam bath for 24 hours, cooled, poured into ice water, and extracted with ether. The ethereal extracts are washed with 10% potassium carbonate solution, water, and dried over sodium sulfate. The solvent is removed under vacuum to give 8.4 g of dark oil, namely, benzo[b]thiophene2-carboxylic acid-3-ethoxy-5-methoxy methyl ester, which is used directly in the next stage.

(B) Mixture of crude ester (8.4 g) from the previous stage, potassium hydroxide (5.4 g) and methanol (150 ml) is treated according to the procedure of Example 1(GB). Recrystallization from acetonitrile gives 6.15 g (58%) of analytically pure product, mp 162°-3° C. (dec).

EXAMPLE 4(B)

Benzo[b]thiophene-2-carboxamide, 3-ethoxy-5-methoxy-N-1H-tetrazol-5-yl-

A mixture of benzo[b]thiophene-2-carboxylic acid, 3-ethoxy-5-methoxy (5.34 g, 0.021 mole), 1,1'-carbonyl-diimidazole (4.12 g, 0.025 mole), 5-aminotetrazole (2.16 g, 0.025 mole), and triethylamine (2.57 g, 0.025 mole) in acetonitrile (200 ml) is treated according to the procedure in Example 1(H). There is obtained 6.7 g of the product, mp 225°-7° C. Recrystallization from methanol gives 6.55 g (96.9%) of analytically pure product, mp 225°-7° C. (dec).

EXAMPLE 5(A)

Benzo[b]thiphene-2-carboxylic acid, 7-methoxyl-3-(1-methylethoxy)-

Treatment of benzo[b]thiophene-2-carboxylic acid, 7-methoxy-methyl ester (James R. Beck, J. Org. Chem., 38 (23), 4086-7 (1973), cites mp 118°-9°.) (14.05 g, 0.059 mole), 2-bromopropane (15.5 g, 0.130 mole) and potassium t-butoxide (7.28 g, 0.065 mole) in dimethyl sulfoxide (180 ml) by the method of Example 2(FA) gives 8.4 g of dark oil, namely, benzo[b]thiophene-2-carboxylic acid, 7-methoxy-3-(1-methylethoxy)methyl ester, which is used directly in the next stage.

Mixture of crude ester (8.4 g) from the previous stage, potassium hydroxide (5 g) and methanol (200 ml) is treated according to the procedure of Example 1(GB). There is obtained 4.68 g of the product, which is recrystallized from acetonitrile to give 3.4 g (21.7%) of analytically pure product, mp 162°-3° C.

EXAMPLE 5(B)

Benzo[b]thiophene-2-carboxamide, 7-methoxy-3-(1-methylethoxy)-N-1H-tetrazol-5-yl- A mixture of benzo[b]thiophene-2-carboxylic acid, 7-methoxy-3-(1-methylethoxy) (2.96 g, 0.011 mole), 1,1'-carbonyldiimidazole (1.8 g, 0.011 mole), and 5-aminotetrazole (0.94 g, 0.011 mole) in tetrahydrofuran (200 ml) is treated according to the procedure in Example 2 (GA). There is obtained 3.8 g of a solid, which is recrystallized from methanol to give 1.6 g (43%) of analytically pure product, mp 228°-230° C. (dec).

EXAMPLE 6(A)

Methyl-5-methylsalicylate (Brederman, Pike, Ber. 6, 324 (1873), bp 236°-7°)

Treatment of 5-methylsalicylic acid (Aldrich) (304.3 g, 2 moles) sodium bicarbonate (168 g, 2 moles) in acetone (2 l) with dimethyl sulfate (252.26 g, 2 moles) by the method of Example 1(A) gives 296.2 g (89%) of analytically pure oil, bp 105°/6 mm.

EXAMPLE 6(B)

Benzoic acid, 5-methyl-2[(dimethylamino)thioxomethoxy]-methyl ester

Treatment of methyl-5-methylsalicylate (250.7 g, 1.50 mole) and 1,4-diazabicyclo[2.2.2]octane (374 g, 3.23 moles) in dimethylformamide (1.2 1) with dimethylthiocarbamoyl chloride (400 g, 3.23 mole) by the method of Example 1(B) gave the product. Two recrystalizations from methanol gives 246.6 g (64.9%) of analytically pure product, mp 102°-3° C.

EXAMPLE 6(C)

Benzoic acid, 5-methyl-2[(dimethylamino)carbonyl)thio]-methyl ester

Treatment of benzoic acid-5-methyl-2[(dimethylamino)thioxomethoxy]methyl ester (263.4 g) in diphenyl ether (2234 g) by the method of Example 1(C) gave a mixture, which is dissolved in hexane and chromatographed on silica gel (789 g). Elution with hexane, first gives diphenyl ether, then elution with methylene chloride gives 160.2 g of viscous oil. Further elution with chloroform yields 10.5 g of analytically pure oil, making the total yield 170.7 g (67.4%).

EXAMPLE 6(D)

5-Methylthiosalicylic acid (F. Knollpfeifer et al, Chem. Ber. 58, 1668 (1925) cites mp 155°-7° (different method)

Hydrolysis of benzoic acid-5-methyl-2[(dimethylamino)carbonyl)thio]methyl ester (170.2 g, 0.67 mole) with sodium hydroxide (70.2 g, 1.7 moles), methanol (940 ml) and water (470 ml) by the method of Example 1(D) gives 107.1 g (94.4%) of analytically pure product, mp 155°-7° C.

EXAMPLE 6(E)

Methyl-5-methylthiosalicylate (Frederic G. Mann et al, J. Chem. Soc., 747 (1951) bp 85-7/0.5 mm, mp 61°-2° (different method)

Treatment of 5-methylthiosalicylic acid (106.6 g, 0.63 mole) with methanol (2.2 1) and sulfuric acid (128 ml) by the method of Example 1(E) gave the product. The solid is dissolved in ether, washed with water, and dried to give 106.3 (92%) of analytically pure product, mp 56°-8° C.

EXAMPLE 6(F)

Benzo[b]thiophene-2-carboxylic acid, 3-hydroxy-5-methyl-, methyl ester

Treatment of methyl 5-methylthiosalicylate (105.6 g, 0.58 mole) in dimethylsulfoxide (600 ml) with potassium-t-butoxide (135 g, 1.2 mole) and methyl chloroacetate (62.9 g, 0.58 mole) by the method of Example 1(F) gave the product. Recrystallization from methanol gives 91.6 g (71.1%) of analytically pure product, mp 93°-4° C.

EXAMPLE 6(G)

Benzo[b]thiophene-2-carboxylic acid, 5-methyl-3(1-methylethoxy)-

(A) Treatment of benzo[b]thiophene-2-carboxylic acid-3-hydroxy-5-methyl-, methyl ester (15 g, 0.067 mole) with O,N,N'-triisopropyl, pseudourea (50.3 g, 0.27 mole) in acetonitrile (250 ml) by the method of Example 1 (GA) gave 17.51 g of dark oil, namely, benzo[b]thiophene-2-carboxylic acid-5-methyl-3(1-methylethoxy)methyl ester, which is used directly in the next stage.

(B) A mixture of crude ester (17.51 g) from the previous stage, potassium hydroxide (7.9 g), and methanol (200 ml) is treated according to the procedure of Example 1 (GB) to give 15.15 g of the product, mp 160°-1° C. (dec).

Recrystallization from acetonitrile gives 12.97 g (76.8%) of analytically pure product, mp 161°-2° C. (dec).

EXAMPLE 6(H)

Benzo[b]thiophene-2-carboxamide, 3-(1-methylethoxy)-5-methyl-N-1H-tetrazol-5-yl

A mixture of benzo[b]thiophene-2-carboxylic acid-5-methyl-3(1-methylethoxy) (8.5 g, 0.034 mole), 1,1'-carbonyldiimidazole (6.62 g, 0.041 mole), 5-aminotetrazole (3.47 g, 0.041 mole), and triethylamine (4.13 g, 0.041 mole) in acetonitrile (300 ml) is treated according to the procedure in Example 1(H). There is obtained 10.32 g of the product, mp 247°-9° C. (dec). Recrystallization from methanol gives 8.17 g (80.8%) of analytically pure product, mp 247°-9° C. (dec).

EXAMPLE 7(A)

Benzo[b]thiophene-2-carboxylic acid-6-chloro, 3-(1-methylethoxy)-

(A) Treatment of benzo[b]thiophene-2-carboxylic acid, 6-chloro, methyl ester (James R. Beck, J. Org. Chem., 38, 4086-7 (1973)) (24.3 g) 0.1 mole), 2-bromopropane (26.32 g, 0.21 mole), and potassium t-butoxide (12.91 g, 0.011 mole) in dimethyl sulfoxide (250 ml) by the method of Example 2(FA) gives 16.1 g (56.5%) of benzo[b]thiophene-2-carboxylic acid, 6-chloro-3-(1-methylethoxy), methyl ester, mp 72°-3°.

(B) A mixture of the ester (15.5 g) from the previous stage, potassium hydroxide (6.5 g) and methanol (160 ml) is treated according to the procedure of Example 1(GB). There is obtained 12.8 g of the product, which is recrystallized from acetonitrile to give 9.46 g (34.9%) of analytically pure product, mp 185°-6° C. (dec).

EXAMPLE 7(B)

Benzo[b]thiophene-2-carboxamide, 6-chloro-3(1-methyl-ethoxy)-N-1H-tetrazol-5-yl

A mixture of benzo[b]thiophene-2-carboxylic acid-6-chloro-3-(1-methylethoxy) (8.05 g, 0.03 mole) 1,1'-carbonyldiimidazole (5.79 g, 0.036 mole), 5-aminotetrazole (3.04 g, 0.036 mole) and triethylamine (3.61 g, 0.036 mole) in acetonitrile (200 ml) is treated according to the procedure in Example 1(H). There is obtained 9.8 g of the product, mp 250°-1° C. (dec). Recrystallization from dimethylformamidemethanol gives 8.4 g (84%) of analytically pure product, mp 249°-251° C. (dec).

EXAMPLE 8(A)

Benzo[b]thiophene-2-carboxylic acid, 3-(1-methyl-ethoxy)

(A) Treatment of benzo[b]thiophene-2-carboxylic acid, methyl ester (Friedlander, Ann, 351, 390 (1907)) (25 g, 0.12 mole), 2-bromopropane (32.5 g, 0.26 mole), and potassium-t-butoxide (15.5 g, 0.14 mole) in dimethyl sulfoxide (200 ml) by the method of Example 2 (FA)

gave 18.63 g of dark oil, namely benzo[b]thiophene-2-carboxlyic acid-3-(1-methylethoxy), methyl ester.

(B) A mixture of the crude ester (18.63 g) from the previous stage, potassium hydroxide (8.5 g) and methanol (180 ml) is treated according to the procedure of Example 1 (GB). There is obtained 13.9 g of the product, which is recrystallized from acetonitrile to give 10.36 g (36.5%) of analytically pure product, mp 135°–7° C.

EXAMPLE 8(B)

Benzo[b]thiophene-2-carboxamide, 3-[1-methylethoxy)-N-1H-tetrazol)-5-yl-1H-imidazole-(1:1) complex A mixture of benzo[b]thiophene-2-carboxylic acid-3-(1-methylethoxy) (10.3 g, 0.044 mole) and 1,1'-carbomyldiimidazole( 7.1 g, 0.044 mole) in tetrahydrofuran (300 ml) is stirred at room temperature for 100 minutes under nitrogen, and then at 49° for three hours. To this solution 5-aminotetrazole (3.72 g, 0.044 mole) is added and the resulting mixture is heated at 48° for three hours, and then stirred at room temperature overnight. Filtration of the resulting solid (13.38 g) and recrystallization from methanol tetrahydrofuran gives 11.3 g (69.8%) of analytically pure product, mp 171°–3° C.

EXAMPLE 8(C)

Benzo[b]thiophene-2-carboxamide, 3-methoxy-N-1H-tetrazol-5-yl-

A mixture of benzo[b]thiophene-2-carboxylic acid, 3-methoxy (Auwers, Ann. 393, 372 (1912), cites mp 171, 173° C.) (15 g, 0.072 mole), 1,1'-carbonyldiimidazole (11.9 g, 0.072 mole), and 5-aminotetrazole (6.12 g, 0.072 mole) in tetrahydrofuran (250 ml) is treated according to the procedure in Example 2 (GA). There is obtained 19.1 g of the product. Recrystallization from dimethylformamide-methanol gives 6.8 g (33.8%) of analytically pure product, mp 214° C. (dec).

EXAMPLE 8(D)

Benzo[b]thiophene-2-carboxylic acid, 3-(1,1-dimethylethoxy)

(A) Treatment of benzo[b]thiophene-2-carboxylic acid-3-hydroxy, methyl ester (10.4 g, 0.05 mole) with N,N'-diisopropyl-0-tertbutyl, pseudourea (Erich Schmidt and Fritz Moosmuller, Ann., 597, 235–40 (1955)) (40 g, 0.02 mole) in acetonitrile (400 ml) by the method of Example 1(G) (except the crude reaction mixture containing unreacted ester is washed with dilute potassium carbonate solution) gave 5.57 g of dark oil, namely, benzo[b]thiophene-2-carboxylic acid-3(1,1-dimethylethoxy)-methyl ester which is used directly in the next stage.

(B) A mixture of the crude ester from the previous stage, potassium hydroxide (5.87 g) and methanol (150 ml) is treated according to the procedure of Example 1(GB) to give 4.43 g of the product. Recrystallization from acetonitrile gives 2.35 g (18.8%) of analytically pure product, mp 129°–131° C.

EXAMPLE 9(B)

Benzo[b]thiophene-2-carboxylic acid, 5-chloro-3-(1-methylethoxy)

5-chlorothiosalicylic acid is synthesized according to a method described by Leon Katz et al, in J. Org. Chem., 18, 1380 (1953), then esterified with methanol-sulfuric acid to methyl-5-chlorothiosalicylate, according to the procedure of Example 1(E).

Reaction with methyl chloroacetate, potassium-t-butoxide in dimethyl sulfoxide gave the desired benzo[b]thiophene-2-carboxylic acid-5-chloro-3-hydroxymethyl ester (Ned D. Heidel, J. Org. Chem. 32, 2678 (1967)), mp 154°–5° C. in 71.4% yield, according to the procedure of Example 1(F).

(A) Treatment of benzo[b]thiophene-2-carboxylic acid, 5-chloro-3-hydroxy-methyl ester (24.27 g, 0.1 mole) with O,N,N'-triisopropyl pseudourea (74.4 g, 0.4 mole) by the method of Example 1(GA), gave on recrystallization from methanol 25 g (88%) of a solid, mp 65°–7°, namely, benzo[b]thiophene-2-carboxylic acid-, 5-chloro-3-(1-methylethoxy)- methyl ester.

(B) A mixture of ester (23.25 g, 0.082 mole) from the previous stage, potassium hydroxide (14.04 g) and methanol (350 ml) is treated according to the procedure of Example 1(GB) to give 21.4 g of the product, mp 193° (dec). Recrystallization from acetonitrile gives 17.5 g (78.9%) of analytically pure product, mp 193°–5° C. (dec).

EXAMPLE 9(C)

Benzo[b]thiophene-2-carboxamide, 3-(1-methylethoxy) 5-chloro-N-1H-tetrazol-5-yl- A mixture of benzo[b]thiophene-2-carboxylic acid-5-chloro-3-(1-methylethoxy) (8.31 g, 0.031 mole), 1,1'-carbonyldiimidazole (6.22 g, 0.038 mole), 5-aminotetrazole (3.26 g, 0.038 mole), and triethylamine (3.88 g, 0.038 mole) in acetonitrile (500 ml) is treated according to the procedure in Example 1(H). There is obtained 10.2 g of the product, mp 237–9 (dec). Recrystallization from methanol gives 7.6 g (73.3%) of analytically pure product, mp 238°–240° C. (dec).

EXAMPLE 10(B)

Benzo[b]thiophene-2-carboxylic acid, 5-methoxy-3-(1,1-dimethylethoxy)

Treatment of benzo[b]thiophene-2-carboxylic acid-5-methoxy-methyl ester with N,N'-diisopropyl0-tertbutyl, pseudourea (reference, Example 1(GA)) in acetonitrile by the method of Example 1(G) (except the crude reaction mixture containing unreacted ester is washed with dilute potassium carbonate solution) gave 7.0 g of dark oil, namely, benzo[b]thiophene-2-carboxylic acid-5-methoxy-3-(1,1-dimethylethoxy)methyl ester. Hydrolysis with methanolic potassium hydroxide, according to the procedure of Example 1(GB) after recrystallization from acetonitrile gives 3.7 g (35.6%) of analytically pure product, mp 145°–7° C. (dec).

EXAMPLE 10(C)

Benzo[b]thiophene-2-carboxamide, 3-(1,1-dimethylethoxy)-5-methoxy-N-1H-tetrazol-5-yl- To a mixture of benzo[b]thiophene-2-carboxylic acid-5-methoxy-3-(1,1-dimethylethoxy) (2.8 g, 0.01 mole), 5-aminotetrazole (0.85 g, 0.01 mole) in tetrahydrofuran (100 ml) is added a solution of 1,3- c diisopropyl carbodiimide (1.3 g, 0.01 mole) in tetrahydrofuran (10 ml), dropwise at 0° under a nitrogen atmosphere. The solution is stirred at 0° for two hours, then at room temperature for 17 hours. The solvent is removed under reduced pressure <30° and the residue is recrystallized from methanol to give 0.8 g of analytically pure product, mp 246°–8° C. (dec).

EXAMPLE 11(B)

Benzo[b]thiophene-2-carboxylic acid,
5-nitro-3-(1-methylethoxy)

(A) Treatment of benzo[b]thiophene-2-carboxylic acid-3-hydroxy-5-nitro-methyl ester (Michael Leou Thominet, U.S. Pat. No. 3,954,748 (1976)) (20.25 g, 0.08 mole) with O,N,N'-triisopropyl, pseudourea (59.6 g, 0.32 mole) in acetonitrile (600 ml) by the method of Example 1(GA) on recrystallization from methylene chloride-methanol gave 13.64 g (57.8%) of analytically pure benzo[b]thiophene-2-carboxylic acid-5-nitro-3-(1-methylethoxy), methyl ester, mp 175°–7° C.

(B) A mixture of the ester from the previous stage (12.57 g, 0.043 mole), potassium hydroxide (7.4 g), and methanol (180 ml) is treated according to the procedure of Example 1(GB) to give 11.82 g of the product, mp 228°–230° (dec). Recrystallization from tetrahydrofuran-acetonitrile, gives 10.95 g (91.5%) of analytically pure product, mp 228°–230° C. (dec).

EXAMPLE 11(C)

Benzo[b]thiophene-2-carboxamide,
3-(1-methylethoxy)-5-nitro-N-1H-tetrazol-5-yl-

A mixture of benzo[b]thiophene-2-carboxylic acid-5-nitro-3-(1-methylethoxy) (10 g, 0.036 mole) 1,1'-carbonyldiimidazole (7.2 g, 0.044 mole), 5-aminotetrazole (3.78 g, 0.044 mole), and triethylamine (4.49 g, 0.044 mole) in acetonitrile (500 ml) is treated according to the procedure in Example 1(H). There is obtained 12.3 g of the product, mp 211°–3° (dec). Recrystallization from dimethylformamide-methanol gives analytically pure product, mp 211°–3° C. (dec).

EXAMPLE 12(A)

Benzo[b]thiophene-2-carboxamide,
3-chloro-N-1H-tetrazol-5-yl-

A solution of 5-aminotetrazole (8.51 g, 0.1 mole) and triethylamine (10.1 g, 0.1 mole) in acetonitrile (100 ml)-tetrahydrofuran (100 ml) is added dropwise to a stirred solution of benzo[b]thiophene-2-carbonyl chloride, 3-chloro (W. B. Wright Jr., et al J. Heterocycl., Chem. 1971, 8(5), 711-14 (23.1 g, 0.1 mole) in acetonitrile (100 ml)-tetrahydrofuran (100 ml) at room temperature. The mixture is stirred an additional 18 hours at room temperature and the precipitate is separated by filtration. The solid is suspended in water (~700 ml), heated on a steam bath, then cooled. The solid is isolated by filtration, washed thoroughly with water, then with ether and dried to give 24 g of a product, mp 277° C. (dec). Recrystallization from dimethylformamidemethanol gives 21.84 g (79.3%) of analytically pure product, mp 275° C. (dec).

EXAMPLE 13(A)

Benzo[b]thiophene-2-carboxamide,5-methoxy-3-(1-methylethoxy)

A mixture of benzo[b]thiophene-2-carboxylic acid, 5-methoxy-3-(1-methylethoxy)(10 g, 0.037 mole) and thionyl chloride (25 ml) is heated on a water bath at 50° C. for 30 minutes and then concentrated under vacuum to remove thionyl chloride. The residue is dissolved in methylene chloride (~350 ml) and added to a stirred mixture of concentrated ammonium hydroxide (250 ml) and methylene chloride (250 ml) at 5°–7° C. After 20 minutes at this temperature, the reaction mixture is stirred at room temperature for 75 minutes. The organic layer is separated, washed with water (2×1.3 l), then diluted with ice-water and acidified with acetic acid. The methylene chloride solution is washed with water and brine and dried to give 8.3 g of a solid. Recrystallization from methanol gives 6.38 g (64%) of analytically pure benzo[b]thiophene-2-carboxamide, 5-methoxy-3-(1-methylethoxy)-; mp 155°–7° C.

EXAMPLE 13(B)

Benzo[b]thiophene-2-carbonitrile,
5-methoxy-3-(1-methylethoxy)-

A mixture of benzo[b]thiophene-2-carboxamide, 5-methoxy-3-(1-methylethoxy) (3.25 g, 0.12 mole) and 1,1'-carbonyldiimidazole (3.96 g, 0.024 mole) in acetonitrile (220 ml) is stirred at room temperature for 80 minutes. Allylbromide (11.8 g, 0.098 mole) is added and the reaction mixture is heated at reflux for 12 hours. Most of the volatiles are removed under reduced pressure and the residue obtained is dissolved in ether and washed successively with dilute hydrochloric acid, water, aqueous sodium bicarbonate and water. The extract is dried over sodium sulfate and the solvent is removed to give 3.2 g of oily residue. The oil is purified by chromatography on silica gel (110 g). Eluting with methylene chloride gives 3.01 g (100%) of a solid, mp 80°–1° C. Recrystallization from hexane gives 2.77 g (92%) of analytically pure benzo[b]thiophene-2-carbonitrile, 5-methoxy-3-(1-methylethoxy); mp 80°–1° C.

EXAMPLE 13(C)

1H-tetrazole,
5-[5-methoxy-3-(1-methylethoxy)benzo[b]-thien-2-yl]-

A mixture of benzo[b]thiophene-2-carbonitrile, 5-methoxy-3-(1-methylethoxy)-, (6.2 g, 0.025 mole) sodium azide (5.39 g, 0.080 mole) and ammonium chloride (4.5 g, 0.080 mole in dimethylformamide (250 ml) is heated in a wax bath at 120°–135° C. for 24 hours. The reaction mixture is then cooled, filtered and dimethylformamide is removed at 60° C. under reduced pressure. The residue is treated with ice-water (700 ml), then acidified with acetic acid. The resulting solid is separated by filtration, washed with water then with ether and dried to give 5.8 g of a solid, mp 190°–2° C. Recrystallization from acetonitrile gives 4.8 g (66.6%) of analytically pure, 1H-tetrazole, 5-[5-methoxy-3-(1-methylethoxy)benzo[b]thien-2-yl]; mp 191°–3° C.

EXAMPLE 14(A)

Benzo[b]thiophene-2-carboxamide, 3-(1-methylethoxy)-

A mixture of benzo[b]thiophene-2-carboxylic acid; 3-(1-methylethoxy)- (32.1 g, 0.13 mole), polyphosphate esters (PPE)(337 g) [Yuichi Kanaoka, et al, Chem. Pharm. Bull. 13(9), 1065-1072 (1965)] and purified chloroform (130 ml) is cooled with dry ice-acetone bath and ammonia (~100 ml) is bubbled in. After stirring at <0° for five hours, then at room temperature for 23 hours, the reaction mixture is refluxed for seven hours, then cooled and treated with 25% aqueous sodium carbonate solution. The products are extracted with chloroform. The organic layer is washed with water and brine and dried. Removal of the chloroform under reduced pressure gives 19.7 g of a residue. Chromatography on basic alumina (427 g), eluting with methylene chloride then chloroform, followed by recrystallization from methanol gives 7.3 g of analytically pure product, namely, benzo[b]thiophene2-carboxamide, 3-(1-methylethoxy)-; mp 162°-4° C.

EXAMPLE 14(B)

Benzo[b]thiophene, 2-carbonitrile-3-(1-methylethoxy)

A mixture of benxo[b]thiophene-2-carboxamide, 3-(1-methylethoxy)(5.95 g, 0.025 mole), 1,1′-carbonyldiimidazole (8.2 g, 0.051 mole) and allyl bromide (24.5 g, 0.2 mole) is treated according to the procedure of Example 13B. There is obtained 5.6 g of oily residue, which is dissolved in hexane and chromatographed on silica gel (120 g). Eluting with methylene chloride gives 5.45 g (99.3%) of benzo[b]thiophene-2-carbonitrile, 3-(1-methylethoxy)-; as an oil, which is used directly in the next stage.

EXAMPLE 14(C)

1H-Tetrazole, 5-[3-(1-methylethoxy)benzo[b]thien-2-yl]

A mixture of benzo[b]thiophene, 2-carbonitrile-3-(1-methylethoxy) (5.26 g, 0.024 mole) from the previous stage, sodium azide (2.14 g, 0.033 mile) and ammonium chloride (1.8 g, 0.033 mole) in dimethylformamide (100 ml) is treated according to the procedure in Example 13C. There is obtained 4.7 g of a solid, mp 185°-7° C. Recrystallization from methanol gives 4.2 g (66.8%) of analytically pure, 1H-tetrazole, 5-[3-(1-methylethoxy)benzo[b]thien-2-yl]-; mp 185°-7° C.

EXAMPLE 15(A)

Benzo[b]thiophene-2-carboxylic acid, 3-[(dimethylamino)thioxomethoxy]-5-methoxy-, methyl ester A solution of dimethylthiocarbamoyl chloride (8.13 g, 0.066 mole) in acetonitrile (100 ml) is added during 10 minutes to a stirred mixture of benzo[b]-thiophene-2-carboxylic acid, 3-hydroxy-5-methoxy-, methyl ester (15.15 g, 0.064 mile) and potassium carbonate (9.1 g, 0.066 mole) in acetonitrile (200 ml) at room temperature. The reaction mixture is then refluxed for 18 hours, cooled, filtered and the solvent is removed at 50° C. on a rotary evaporator under reduced pressure. The residue is dissolved in ether and the solution is washed successively with water, cold 8% hydrochloric acid, water, cold sodium bicarbonate solution and water. The organic phase is dried and concentrated to afford 20.7 g of a solid. Recrystallization from methanol gives 16.4 g (79.3%) of analytically pure benzo[b]thiophene-2-carboxylic acid, 3-[(dimethylamino)thioxomethoxy]-5-methoxy-, methyl ester; mp 136°-8° C.

EXAMPLE 15(B)

Benzo[b]thiophene-2-carboxylic acid, 3-[((dimethylamino)carbonyl)thio]-5-methoxy-, methyl ester A solution of benzo[b]thiophene-2-carboxylic acid, 3-[(dimethylamino)thioxomethoxy]-5-methoxy-, methyl ester (14.49 g) in diphenyl ether (240 g) is heated in a wax bath at 230°-247° C. under an atmosphere of nitrogen for 21 hours. After cooling the mixture is dissolved in hexane and chromatographed on silica gel (430 g). The column is successively eluted with hexane, methylene chloride and chloroform. The chloroform is removed under reduced pressure to give 12.48 g of a solid. Recrystallization from methanol gives 9.95 g (69.1%) of analytically pure benzo[b]thiophene-2-carboxylic acid, 3-[((dimethylamino)carbonyl) thio]-5-methoxy-, methyl ester; mp 105°-7° C. methyl ester; mp 105°-7° C.

EXAMPLE 15(C)

3-mercapto 5-methoxybenzo[b]thiophene-2-carboylic acid

A mixture of benzo[b]thiophene-2-carboxylic acid, 3-[((dimethylamino)carbonyl)thio]-5-methoxy-, methyl ester (9.35 g, 0.029 mole), sodium hydroxide (2.9 g), water (40 ml), and methanol (40 ml) is refluxed with stirring under nitrogen for six hours. Most of the methanol is then removed under reduced pressure at 50° C. The residue is dissolved in water (250 ml) and decolorized with activated charcoal. After cooling the solution is carefully acidified with dilute hydrochloric acid, while the temperature is maintained below 15° C. and extracted with ether. The extracts are washed with water and brine, dried and concentrated to give 6.0 g of a residue. Recrystallization from acetonitrile gives 3.4 g (49.3%) of 3-mercapto 5-methoxybenzo[b]thiophene-2-carboxylic acid; mp 148°-150° C. (dec), which is used directly in the next stage.

EXAMPLE 15(D)

1-methylethyl 5-methoxy-3-[(1-methylethyl)thio]benzo[b]thiophene-2-carboxylate

A mixture of 3-mercapto-5-methobenzo[b]thiophene2-carboxylic acid (3.2 g, 0.013 mile) and N,N′, O-triisopropyl, psudourea (20.4 g, 0.11 mole) in acetonitrile (200 ml) is refluxed with stirring under nitrogen for 20 hours. The solvent and volatiles are removed under vacuum and then under high vacuum. The residue is dissolved in methylene chloride and filtered on a silica gel column (115 g) to give 3.37 g (78.4%) of 1-methylethyl, 5-methoxy-3-[(1-methylethyl)thio]benzo[b]thiophene-2-carboxylate; as an oil, which is used directly in the next stage.

EXAMPLE 15(E)

Benzo[b]thiophene-2-carboxylic acid, 5-methoxy-3-[(1-methylethyl)thio]-

A mixture of benzo[b]thiophene-2-carboxylic acid, 5-methoxy-3-[(1-methylethyl)thio]-, methylethyl ester (3.37 g, 0.01 mole), potassium hydroxide (3 g) and methanol (80 ml) is refluxed under nitrogen for three hours. Most of the methanol is removed under reduced pressure at 45° C. The residue is dissolved in hot water (~500 ml) and decolorized with activated charcoal. After cooling the basic solution is carefully acidified with dilute hydrochloric acid. The crystalline precipitate is filtered, washed with water, then dissolved in ether and dried over sodium sulfate. The solvent is removed under reduced pressure to give 2.65 g 90.4% of benzo[b]thiophene2-carboxylic acid, 5-methoxy-3-[(1-methylethyl)thio]-, mp 151°-2° C., which is used directly in the next stage.

EXAMPLE 15(F)

Benzo[b]thiophene-2-carboxamide, 5-methoxy-3-[(1-methylethyl) thio-N-1H-tetrazol-5-yl]

A mixture of benzo[b]thiophene-2-carboxylic acid, 5-methoxy-3-[(1-methylethyl)thio]- (2.5 g, 0.0085 mole) and 1,1′-carbonyldiimidazole (1.72 g, 0.011 mole) in acetonitrile (150 ml) is refluxed with stirring under nitrogen for 100 minutes. A solution of 5-aminotetrazole (0.9 g, 0.011 mole) and triethylamine (1.07 g, 0.011 mole) in acetonitrile (100 ml) is added dropwise. The mixture is heated at reflux for 17 hours, then most of the acetonitrile is removed under water aspirator pressure at 40° C. The residue is treated with cold water (~500 ml), acidified with acetic acid (3.4 ml) and stirred. The resulting solid is separated by filtration, washed with water, then with ether and dried to give 2.4 g of a solid. Recrystallization from methanol gives 1.7 g (55%) of analytically pure benzo[b]thiophene-2-carboxamide, 5-methoxy-3-[(1methylethyl)thio-$\underline{N}$-1$\underline{H}$-tetrazol-5-yl]-; mp 236° C. (dec).

EXAMPLE 16

Examples 16(A-F) are prepared by the methods of Examples 15(A-F) and are found in Table 1.

TABLE 1

| Example | R | $R_1$ | Yield % | MP °C. | Recrystallization solvent |
|---|---|---|---|---|---|
| 16(A) | $CO_2CH_3$ | $-OCN(CH_3)_2$ $\|\|$ $O$ | 48.3 | 160–1 | methylene chloride-methanol |
| 16(B) | $CO_2CH_3$ | $-SCN(CH_3)_2$ $\|\|$ $O$ | 62.7 | 178–80 | methylene chloride-methanol |
| 16(C) | $CO_2H$ | $-SH$ | 68.9 | 185° (dec) | diethyl ether |
| 16(D) | $CO_2CH(CH_3)_2$ | $-SCH(CH_3)_2$ | 88.3 | oil | |
| 16(E) | $CO_2H$ | $-SCH(CH_3)_2$ | 70 | 140–1 | Acetonitrile |
| 16(F) | CNH— $\|\|$ O tetrazole | $-SCH(CH_3)_2$ | 51 | 255° (dec) | dimethylformamide-methanol |

EXAMPLE 16(F)

Benzo[b]thiophene-2-carboxamide, 3-[(1-methylethyl)thio]N-1H-tetrazol-5-yl-

Procedure A

5-Methoxy-2-(2-methoxy-2-oxoethoxy)benzoic acid, methyl ester

A mixture of 50.0 g (0.27 mole) of 2-hydroxy-5-methoxybenzoic acid, methyl ester, 88.0 g (0.64 mole) of anhydrous potassium carbonate, and 25.4 ml (46.4 g, 0.30 mole) of methyl bromoacetate in 300 ml of N,N-dimethylformamide is stirred at room temperature for 24 hours. The reaction mixture is added to 1100 g of ice/water, stirred for 1 hour, and the precipitated crude product is filtered and washed with water. Recrystallization from aqueous methanol yields 54.7 g (78% yield) of analytically pure 5-methoxy-2-(2-methoxy-2-oxoethoxy) benzoic acid, methyl ester, mp 82°–85° C.

The following compounds are prepared in a manner analogous to the above procedure A using corresponding starting materials.

2-(2-methoxy-2-oxoethoxy)-5-phenylbenzoic acid, methyl ester, mp 66°–68.5° C.

2-(2-methoxy-2-oxoethoxy)-3-phenylbenzoic acid, methyl ester, mp <30° C.

4-methoxy-2-(2-methoxy-2-oxoethoxy)benzoic acid, methyl ester, mp 74°–77° C. (See the J. D. Brewer, et al, reference cited above.)

3-methoxy-2-(methoxy-2-oxoethoxy)benzoic acid, methyl ester, mp 73°–74° C.

3-(2-methoxy-2-oxoethoxy)-2-naphthalenecarboxylic acid, methyl ester, mp 70°–72° C.

Procedure B

2-Cyanomethoxy-3-methoxybenzoic acid, methyl ester

A mixture of 57.1 g (0.31 mole) of 2-hydroxy-3-methoxybenzoic acid, methyl ester, 95.5 g (0.69 mole) of anhydrous potassium carbonate, and 23.9 ml (28.5 g; 0.38 mole) of chloroacetonitrile in 260 ml of N,N-dimethylformamide is heated on the steam bath for three hours. The mixture is cooled, added to 1700 g of ice/water, stirred for 1 hour, and the precipitated crude product is filtered and washed with water. Recrystallization from aqueous methanol yields 52.5 g 77% yield) of the 2-cyanoethoxy-3-methoxybenzoic acid, methyl ester, mp 77°–78° C. (See U.S. Pat. No. 4,420,476 for mp of 74°–75° C.)

The following compounds are prepared in a manner analogous to procedure B above using corresponding starting materials.

2-Cyanomethoxy5-methoxybenzoic acid, methyl ester, mp 58°–59.5° C.

2-Cyanomethoxy-4-methoxybenzoic acid, methyl ester, mp 59°–64° C.

Additionally, using a procedure disclosed by S. S. Sangapure and Y. S. Agasimundin, in *Ind. J. Chem.*, 14B, 6886 (1976) the following compounds were prepared.

2-cyanomethoxybenzoic acid ethyl ester, mp 54°–56° C.

2-cyanomethoxybenzonitrile, mp 64°–66° C.

Both of the melting points of these compounds are consistent with those reported for the compounds by K. Gewand and H-J. Jansch, in *J. prakt. Chem;* 315, 779 (1973).

Procedure C

3-Hydroxynaphtho[2,3-b]furan-2-carboxylic acid, methyl ester

A solution of sodium methoxide is prepared by adding 5.6 g (0.24 mole) of sodium metal in portions to 350 ml of methanol (under a nitrogen atmosphere). The solution is stirred while 47.0 g (0.17 mole) of 3-(2-methoxy-2-oxoethoxy)-2-naphthalenecarboxylic acid, methyl ester is added, followed by an additional 130 ml of methanol. The mixture is stirred at reflux for 4.5 hours, cooled, and added to 1.0 kg of ice/water. Acidification with glacial acetic acid precipitates the crude furan product, which is filtered and washed with water. Recrystallization from ethanol yields 26.9 g (65% yield) of analytically pure 3-hydroxynaphtho2,3-b]furan-2-carboxylic acid, methyl ester, mp 158°–160° C.

The following compounds are prepared in a manner analogous to Procedure C. above using corresponding starting materials.

3-hydroxy-5-phenylbenzofuran-2-carboxylic acid, methyl ether, mp 167°–169 ° C.

3-hydroxy-7-phenyl-2-benzofurancarboxylic acid, methyl ester, mp 158°–160° C.

3-hydroxy-5-methoxy-2-benzofurancarboxylic acid, methyl ester, mp 181°–184° C.

3-hydroxy-7-methoxy-2-benzofurancarboxylic acid, methyl ester, mp 113°–115° C.

Procedure D

3-Hydroxy-6-me thoxy-2-benzofurancarboxylic acid, methyl ester

A mixture of 10.4 g (0.093 mole) of potassium tert-butoxide in 175 ml of toluene (under a nitrogen atmosphere) is stirred and cooled in a cold water bath. A solution of 18.1 g (0.071 mole) of 4-methoxy-2-(2-methoxy-2-oxoethoxy) benzoic acid, methyl ester is added over 80 minutes. The mixture is stirred and heated on the steam bath for three hours, then cooled and added to 600 g of ice/water. The organic layer is separated, washed with water (2×100 ml), and the aqueous washes are combined with the original aqueous layer. The combined aqueous layers are washed with dichloromethane (2×250 ml), then filtered. The filtrate is cooled in ice and acidified with glacial acetic acid to precipitate the crude product, which is filtered and washed with water. Recrystallizatin from aqueous methanol yields 8.5 g 54% yield) of the 3-hydroxy-6-methoxy-2-benzofurancarboxylic acid methyl ester product, mp 93°–95 ° C. (mp of 80°–85° C. is reported in the J. D. Brewer, et al reference cited above).

The following compunds are prepared in a manner analogous to Procedure D above using corresponding starting materials.

3-hydroxy-5-methoxy-2-benzofurancarbonitrile, mp 166° C. (dec). The melting point of this compound is disclosed to be 184° C. in the British patent No. 1,233,268 cited above.

3-hydroxy-6-methoxy-2-benzofurancarbonitrile, mp 160°–161° C.

3-hydroxy-7-methoxy-2-benzofurancarbonitrile, mp 181°–182° C. A melting point of 176°–178° C. is reported by K. Gewand and H. J. Jansch in *J. Prakt. Chem.*, 315, 779 (1973) also cited above.

Additionally, the following compounds were prepared as indicated.

3-amino-2-benofurancarboxylic acid, ethyl ester, mp 76°–78° C. (prepared by the procedure of K. Gewand and H-J. Jansch, *J. Prakt. Chem.*, 315, 779 (1973) and having a melting point consistent with that reported by S.S. Sangapure and Y. S. Agasimundin, *Ind. J. Chem.*, 14B, 6886 (1976)).

3-amino-2-benzofurancarbonitrile, mp 159°–161.5° C. (prepared by the procedure reported by S.S. Sangapure and Y. S. Agasimundin cited above but reporting a mp of 149° C.

Procedure E

3-Methoxynaphtho[2,3-b]furan-2-carboxylic acid, methyl ester

A mixture of 25.0 g (0.10 mole) of 3-hydroxynaphtho[2,3-b]furan-2-carboxylic acid, methyl ester, 15.3 g (0.11 mole) of anhydrous potassium carbonate, and 10.6 ml (14.1 g, 11 mole of dimethyl sulfate in 500 ml of acetone is stirred at refux for 24 hours. The mixture is cooled, filtered, and the filter cake is washed several times with fresh acetone. The combined filtrates are evaporated (vacuum), and the residue is recrystallized from methanol to yield 20.3 g (77% yield) of the analytically pure 3-methoxynaphtho[2,3-b]furan-2-carboxylic acid, methyl ester, mp 121°–124 ° C.

Replacement of the dimethyl sulfate in the above procedure with diethyl sulfate yielded th ethoxy-esters.

The following additional alkoxy-esters are also prepared by this procedure from the corrosponding hydroxy-esters:

3-methoxy-5-phenyl-2-benzofurancarboxylic acid, methyl ester, 3-ethoxy-5-phenyl-2-benzofurancarboxylic acid, methyl ester, 3-methoxy-7-phenyl-2-benzofurancarboxylic acid, methyl ester, and 3-ethoxy-7-phenyl-2-benzofurancarboxylic acid, methyl ester.

These compounds are used as oils without extensive purification for conversion to the corresponding carboxylic acids.

Additional compounds as follows are prepared in the same manner as procedure E using corresponding appropriate starting materials.

3,5-dimethoxy-2-benzofurancarboxylic acid, methyl ester, mp 108°–110° C.;

3,6-dimethoxy-2-benzofurancarboxylic acid, methyl ester, mp 71°–74° C. (mp of 63°–65° C. was reported for this compound by J. D. Brewer, et al, cited above); and, 3,7-dimethoxy-2-benzofurancarboxylic acid methyl ester, mp 71°–73° C.

Procedure F

5-Methoxy-3-(1-methylethoxy)-2-benzofurancarboxylic acid, methyl ester

A solution of 12.3g (0.11 mole) of potassium tert-butoxide in 100 ml of dimethyl sulfoxide (under a nitrogen atmosphere) is cooled in a cold water bath and treated dropwise with a solution of 16.6 g (0.075 mole) of 3-hydroxy-5-methoxy-2-benzofuran carboxylic acid, methyl ester. The mixture is stirred for 45 minutes after completion of the addition, and 7.0 ml (9.2 g; 0.075 mole) of 2-bromopropane is added in one portion. After stirring for 24 hours at room temperature, the reaction mixture is added to 1.5 kg of ice/water and stirred an additional hour. The precipitated product is filtered and washed with water. The crude yield is 9.0 g (46% yield). A sample recrystallized from aqueous methanol yields analytically pure 5-methoxy-3-(1-methylethoxy)-2-benzofurancarboxylic acid methyl ester, mp 66°–68° C.

Replacement of the 2-bromopropane in the above procedure with other alkylating agents (such as dimethyl sulfate) permits preparation of the corresponding alkoxy-esters.

The following additional alkoxy-esters are also prepared by this procedure from the appropriate hydroxy-esters:

3-(1-methylethoxy)-5-phenyl-2-benzofurancarboxylic acid, methyl ester, 3-(1-methylethoxy)-7-phenyl-2-benzofurancarboxylic acid, methyl ester, 7-methoxy-3-(nonyloxy)-2-benzofurancarboxylic acid, methyl ester, and 6-methoxy-3-(1-methylethoxy)-2-benzofuran carboxylic. acid, methyl ester.

These compounds are used as oils without extensive purification for conversion to the corresponding carboxylic acids.

Additionally, the following compounds are prepared according to the procedure F above using appropriate corresponding starting materials.

7-methoxy-3-(1-methylethoxy)-2-benzofurancarboxylic acid methyl ester m.p. 53°–55° C.;

3,5-dimethoxy-2-benzofuran carbonitrile, mp 118°–120° C.;

3,6-dimethoxy-2-benzofuran carbonitrile, mp 139°–140° C.;

3,7-dimethoxy-2-benzofuran carbonitrile, mp 106°–109° C.

Procedure G

5-Methoxy-3-(phenylmethoxy)-2-benzofurancarboxylic acid, methyl ester

A mixture of 8.0 g (0.036 mole) of 3-hydroxy-5-methoxy-2-benzofurancarboxylic acid, methyl ester and 10.0 g (0.043 mole) of O-phenylmethoxy-N,N'-diisopropylisourea (L. J. Mathias, *Synthesis*, 561 (1979)) in 200 ml of acetonitrile is stirred at reflux under a nitrogen atmosphere for 22 hours. The mixture is cooled and filtered to remove by-product 1,3-diisopropylurea. The insoluble material is washed with hexane and the combined filtrates are evaporated (vacuum). The residue is treated with 250 ml of diethyl ether, and the mixture is again filtered and evaporated. The crude oil residue is chromatographed over silica gel using dichloromethane/hexane (2:1) elution to obtain 7.2 g 64% yield) of the purified 5-methoxy-3-(phenylmethoxy)2-benzofurancarboxylic acid, methyl ester as an oil. The ester is saponified without additional purification.

Also prepared by the above procedure is 6-methoxy-3-(phenylmethoxy)-2-benzofurancarboxylic acid, methyl ester, mp 81°–84° C.

Procedure H 3-(Acetylamino)-2-benzofurancarbonitrile

A solution of 3.86 g (0.024 mole) of 3-amino-2-benzofurancarbonitrile in 50 ml of pyridine is cooled in ice and treated over 15 minutes with 2.0 ml (2.21 g; 0.028 mole) of acetyl chloride. The mixture is stirred in ice an additional two hours and added to 250 g of ice/water. The precipitated crude product is filtered, washed with water, and recrystallized from aqueous methanol to yield 2.8 g (57% yield) of 3-(acetylamino)-2-benzofurancarbonitrile. A sample recrystallized a second time as above is analytically pure, mp 187°–189° C.

Additionally, the following compound is prepared according to Procedure H using appropriate, corresponding starting material.

3-(acetylamino)-2-benzofurancarboxylic acid, ethyl ester, mp 164°–167° C. (S. B. Mahajan and Y. S. Agasimundin cited above reported a melting point of 166° C. for this compound).

Procedure I 3,5-Dimethoxy-2-benzofurancarboxylic acid

A mixture of 10.6 g (0.045 mole) of 3,5-dimethoxy-2-benzofurancarboxylic acid, methyl ester in 80 ml of methanol is treated with 75 ml of 1.0 N aqueous sodium hydroxide solution. The new mixture is stirred at reflux for 45 minutes, cooled, and added to 750 g of ice/water. After extraction with dichloromethane, 3×300 ml) the aqueous layer is cooled in ice and acidified with glacial acetic acid to precipitate the crude product. The precipitate is filtered and washed with water to yield 9.6 g (88% crude yield) of 3,5-dimethoxy-2-benzofurancarboxylic acid. A sample recrystallized from ethyl acetate is analytically pure, mp 168° C.-dec.

Additionally, the following compounds are prepared according to procedure I using appropriate corresponding starting materials.

3-methoxy-5-phenyl-2-benzofurancarboxylic acid, mp 190°–191° C.;

3-ethoxy-5-phenyl-2-benzofurancarboxylic acid, mp 168°–170° C.;

3-(1-methylethoxy)-5-phenyl-2-benzofurancarboxylic acid, mp 170°–170.5° C.;

3-methoxy-7-phenyl-2-benzofurancarboxylic acid, mp 175°–178° C.;

3-ethoxy-7-phenyl-2-benzofurancarboxylic acid, mp 165°–166° C.;

3-(1-methylethoxy)-7-phenyl-2-benzofurancarboxylic acid, mp 180°–182° C.;

3-(1-methyethoxy)-5-methoxy-2-benzofurancarboxylic acid, mp 136°–138° C.;

5-methoxy-3-phenylmethoxy-2-benzofurancarboxylic acid, mp 173° C.-dec.;

3,6-dimethoxy-2-benzofurancarboxylic acid, mp 145° C.-dec.;

3-(1-methylethoxy)-6-methoxy-2-benzofurancarboxylic acid, mp 120° C.-dec.;

3,7-dimethoxy-2-benzofurancarboxylic acid, mp 189°–190° C.;

3-(methylethoxy)-7-methoxy-2-benzofurancarboxylic acid, mp 128°–129° C.:

3-acetylamino-2-benzofurancarboxylic acid, mp 208° C.-dec. (F. A. Trofimov, et al, cited above reported a mp of 210° C.-dec. for this compound);

3-methoxynaphtho[2,3-b]furan-2-carboxylic acid, mp 220° C.-dec;

6-methoxy-3-phenylmethoxy-2-benzofurancarboxylic acid, mp 140° C.-dec.

Procedure J

7-Methoxy-3-(nonyloxy)-2-benzofurancarboxylic acid

A mixture of 1.34 g (0.012 mole) of potassium tert-butoxide in 50 ml of dimethyl sulfoxide (under a nitrogen atmosphere) is treated with 2.3 g (0.0066 mole) of crude 7-methoxy-3-(nonyloxy)-2-benzofurancarboxylic acid, methyl ester. After stirring at room temperature for three hours, the mixture is added to 400 g of ice/water. The new mixture is extracted with dichloromethane (3×250 ml), and the aqueous layer is cooled in ice and acidified with 4.0 N hydrochloric acid. The semisolid precipitate that forms is removed by extracting with dichloromethane (3×150 ml). The combined extracts are backwashed with water (2×200 ml), dried (anhydrous sodium sulfate), and evaporated (vacuum) to yield 7-methoxy-3-(nonyloxy)-2-benzofurancarboxylic acid (0.7 g; 32% yield) as an oil. The crude oil is converted to the corresponding 2-benzofurancarbamoyltetrazole without further purification.

Procedure K

3-Methoxy-5-phenyl-N-1e,uns/H/ -tetrazol-5-yl-2-benzofurancarboxamide

A mixture of 0.90 g (0.0034 mole) of 3-methoxy-5-phenyl-2-benzofurancarboxylic acid and 0.55 g (0.0034 mole) of 1,1-carbonylbis(1H-imidazole) in 25 ml of tetrahydrofuran is stirred at reflux for one hour. To the mixture is added 0.29 g (0.0034 mole) of anhydrous 5-aminotetrazole, and the new mixture is stirred at reflux for an additional 16 hours. Cooling to room temperature results in precipitation of 3-methoxy-5-phenyl-N-1e,uns/H/ -tetrazol-5-yl-2-benzofurancarboxamide. The precipitate is filtered and recrystallized from methanol to yield 0.90 g 80% yield) of analytically pure tetrazole, mp 260°–262° C.

In an analogous manner as found above in Procedure K, the following compounds are prepared using appropriate corresponding starting materials.

3-ethoxy-5-phenyl-N-1H-tetrazol-5-yl-2-benzofurancarboxamide, mp 263°–266° C.;

3-(1-methylethoxy)-5-phenyl-N-1H-tetrazol-5-yl-2-benzofurancarboxamide, mp 253°–254° C.;

3-methoxy-7-phenyl-N-1H-tetrazol-5-yl-2-benzofurancarboxamide (1:1 complex with imidazole), mp 214°–215° C.;

3-ethoxy-7-phenyl-N-1H-tetrazol-5-yl-2-benzofurancarboxamide (1:1 complex with imidazole), mp 214°–216° C.;

3-(1-methylethoxy)-7-phenyl-N-1e,uns/H/ -tetrazol-5-yl-2-benzofurancarboxamide (1:1 complex with imidazole), mp 224°–227° C.

Procedure L 3,6-Dimethoxy-N-1H-tetrazol-5-yl-2-benzofurancarboxamide

A mixture of 5.0 g (0.023 mole) of 3,6-dimethoxy-2-benzofurancarboxylic acid and 8.0 g (0.049 mole) of 1,1-carbonylbis(1H-imidazole) in 60 ml of N,N-dimethylformamide is stirred and warmed on the steam bath for 20 minutes. The mixture is cooled to room temperature, 2.5 g (0.024 mole) of 5-aminotetrazole monohydrate is added, and the new mixture is again heated for 20 minutes. The reaction mixture is cooled, added to 350 g of ice/water and acidified with 4.0 N hydrochloric acid to precipitate the tetrazole product. The precipitate is filtered, washed with 50% aqueous ethanol, and recrystallized from aqueous N,N-dimethylformamide to yield 2.8 g (43% yield) of the analytically pure 3,6-dimethoxy-N-1e,uns/H/ tetrazol-5-yl-2-benzofurancarboxamide, mp 238° C.-dec.

In an analogous manner as found above in Procedure L the following compounds are prepared using appropriate corresponding starting materials.

3,5-dimethoxy-N-1e,uns/H/ -tetrazol-5-yl-2-benzofurancarboxamide, mp 243° C.-dec.;

3,6-dimethoxy-N-1e,uns/H/ -tetrazol-5-yl-2-benzofurancarboxamide, mp 238° C.-dec.;

3,7-dimethoxy-N-1e,uns/H/ -tetrazol-5-yl-2-benzofurancarboxamide, mp 235°–238° C.;

3-nonyloxy-7-methoxy-N-1e,uns/H/ -tetrazol-5-yl-2-benzofurancarboxamide, mp 207°–209° C.;

3-acetylamino-N-1e,uns/H/ -tetrazol-5-yl-2-benzofurancarboxamide, mp 275° C.-dec.;

3-methoxy-N-(1e,uns/H/ -tetrazol-5-yl)naphtho[2,3-b]furan-2-carboxamide, mp 250° C.-dec.

Procedure M

5-Methoxy-3-(1-methylethoxy)-N-1H-tetrazol-5-yl-2-benzofurancarboxamide

A mixture of 5.7 g (0.023 mole) of 5-methoxy-3-(1-methylethoxy)-2-benzofurancarboxylic acid and 4.2 g (0.026 mole ) of 1,1-carbonylbis(1H-imidazole) in 140 ml of acetonitrile is stirred at reflux for one hour. The mixture is cooled, treated with 2.3 g (0.027 mole) of anhydrous 5-aminotetrazole plus 7.7 ml (5.6 g; 0.055 mole) of triethylamine, and heated at reflux for an additional five hours. The cooled reaction mixture is added to 1.5 kg of ice/water and acidified with glacial acetic acid to precipitate the tetrazole product. The precipitate is filtered, washed with water, and recrystallized from aqueous acetonitrile to yield 6.0 g (82% yield) of the analytically pure 5-methoxy3-tetrazol-5-yl-2-benzofurancarboxamide, mp 241°–245° C.

In an analogous manner as described above in Procedure M the following compounds are prepared using appropriate corresponding starting materials.

5-methoxy-3-phenylmethoxy-N-1e,uns/H/ -tetrazol-5-yl-2-benzofurancarboxamide, mp 205° C.-dec;

6-methoxy-3-phenylmethoxy-N-1e,uns/H/ -tetrazol-5-yl-2-benzofurancarboxamide, mp 210° C.-dec;

6-methoxy-3-(1-methylethoxy)-N-1e,uns/H/ -tetrazol-5-yl-2-benzofurancarboxamide, mp 231° C.-dec;

7-methoxy-3-(1-methyethoxy)-N-1e,uns/H/ -tetrazol-5-yl-2-benzofurancarboxamide, mp 180°–190° C.

Procedure N

3-Amino-N-1H-tetrazol-5-yl-2-benzofurancarboxamide

A mixture of 5.3 g (0.019 mole) of 3-(acetylamino)N-1e,uns/H/ -tetrazol-5-yl-2-benzofurancarboxamide in 50 ml of ethanol plus 50 ml of concentrated (12.0 M) hydrochloric acid is stirred at reflux for two hours. The reaction mixture is cooled in ice to precipitate 3-amino-N-1e,uns/H/ -tetrazol-5-yl-2-benzofurancarboxamide. The precipitate is filtered, washed with 50% aqueous ethanol, and recrystallized from aqueous 2-methoxyethanol to yield 2.4 g (53% yield) of the analytically pure 3-amino-N-1e,uns/H/ -tetrazol-5-yl-2-benzofurancarboxamide, mp 275° C.-dec.

In an analogous manner as described above in Procedure N using appropriate corresponding starting materials the following compound is prepared.

5-(3-amino-2-benzofuranyl)-1e,uns/H/ -tetrazole, mp 185° C.-dec.

Procedure O 5-(3,6-Dimethoxy-2-benzofuranyl)-1H-tetrazole

A mixture of 3.8 g (0.019 mole) of 3,6-dimethoxy-2-benzofurancarbonitrile, 3.4 g (0.052 mole) of sodium azide and 2.8 g (0.052 mole) of ammonium chloride in 40 ml of N,N-dimethylformamide is stirred and heated (under a nitrogen atmosphere ) on the steam bath for four hours. The mixture is cooled, added to 400 g of ice/water, and acidified with glacial acetic acid to precipitate 5-(3,6-dimethoxy-2-benzofuranyl)-1e,uns/H/ -tetrazole. The precipitate is filtered, washed with water, and recrystallized from ethyl acetate to yield 2.0 g (43% yield) of the analytically pure tetrazole product, mp 182°–184° C.

In an analogous manner as described above in Procedure O using appropriate corresponding starting materials the following compounds are prepared.

5-(3,5-dimethoxy-2-benzofuranyl)-1e,uns/H/ -tetrazole, mp 216° C.-dec.;

5-(3,7-dimethoxy-2-benzofuranyl)-1H-tetrazole, mp 203°–205° C.;

5-(3-acetylamino-2-benzofuranyl)-1H-tetrazole, mp 237° C.-dec.

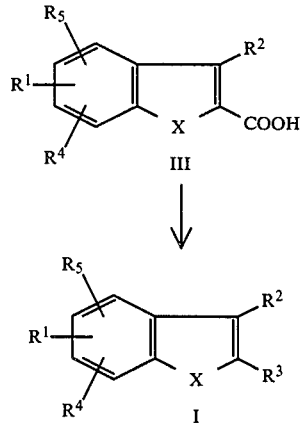

SCHEME I

SCHEME II
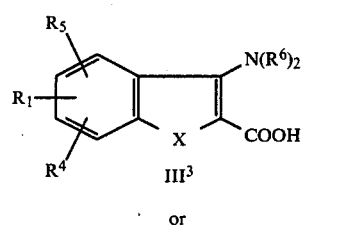
or
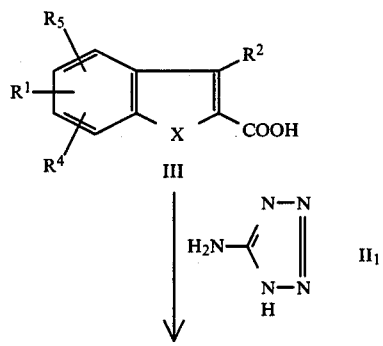
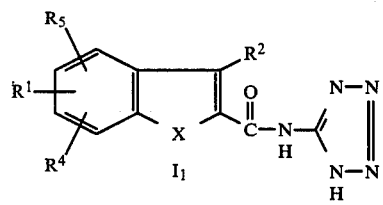
SCHEME III
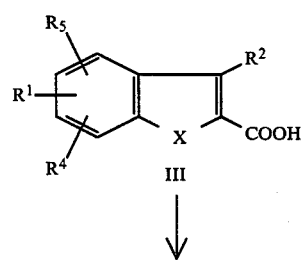
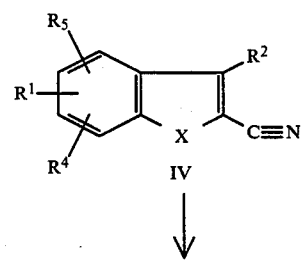
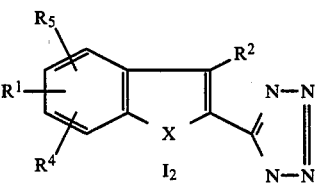
SCHEME IV
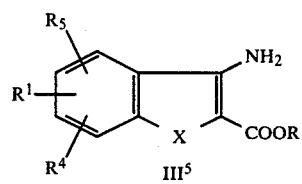
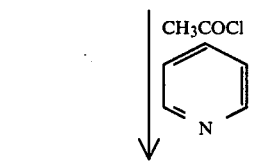
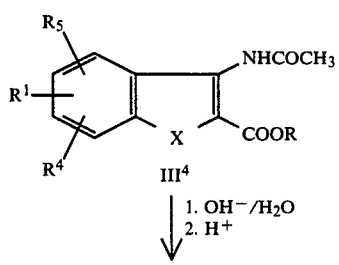
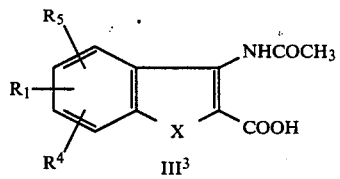
SCHEME V
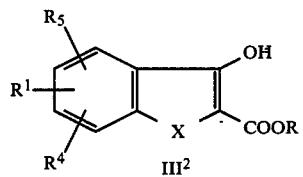
wherein R is alkyl of from one to four carbon atoms.
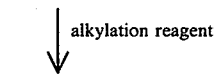 alkylation reagent
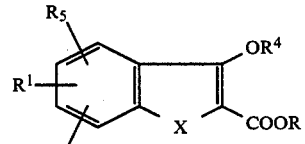
wherein $R^4$ is alkyl of from one to 12 carbon atoms, arylmethyl.
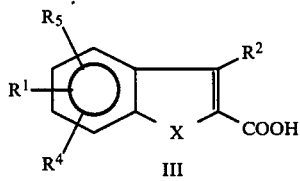
wherein $R^2$ is $OR^4$

FORMULA

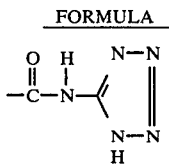
A

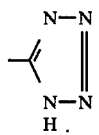
B

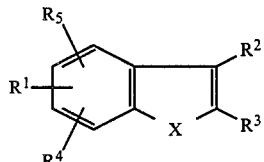
I

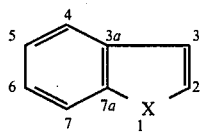
I'

We claim:
1. A compound having the formula:

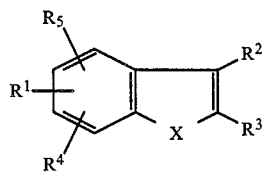
I wherein (1) $R^1$, $R^4$, and $R^5$ are H, alkyl of from one to twelve carbons, inclusive, alkoxy of from one to twelve carbons, inclusive, hydroxy, aryl, $R^1$ taken twice having each an adjacent carbons such that two $R^1$s together are methylenedioxy, nitro, amino, substituted amino, mercapto, alkylthio of from one to four carbons, inclusive, alkylsulfinyl of from one to four carbons, inclusive, alkysulfonyl for from one to four carbons, inclusive, arylthio, arylsulfinyl, arylsufonyl, or halogen; (2) $R^2$ is alkoxy of from one to twelve carbons, inclusive, arylmethoxy, amino, substituted amino, mercapto, alkylthio of from one to four carbons, inclusive alkylsulfinyl of from one to four carbons, inclusive, alkylsulfonyl of from one to four carbons, inclusive, arylthio, arylsulfinyl, or arylsulfonyl; and (3) $R^3$ is A or B

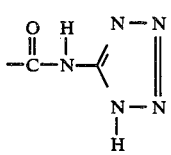
A or

-continued

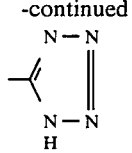
B and (4) X is oxygen or S(O)q wherein q is zero, one, or two; and pharmaceutically acceptable salts thereof.

2. A compound according to claim 1 wherein X is sulfur.

3. A compound according to claim 1 wherein X is oxygen.

4. A compound according to claim 2 wherein $R^3$ is A as defined in claim 1.

5. A compound according to claim 2 wherein $R^3$ is B as defined in claim 1.

6. A compound according to claim 4 wherein the compound is 5-methoxy-3-(1-methylethoxy)-N-1H-tetrazol-5-yl-benzo[b]thiophene-2-carboxamide.

7. A compound according to claim 6 wherein the compound is the arginine salt.

8. A compound according to claim 6 wherein the compound is the sodium salt.

9. A compound according to claim 4 wherein the compound is 3-ethoxy-5-methoxy-N-1e,uns/H/ -tetrazol-5-yl-benzo[b]thiophene-2-carboxamide.

10. A compound according to claim 4 wherein the compound is 7-methoxy-3-(1-methylethoxy)-N-1e,uns/H/ -tetrazol-5-yl-benzo[b]thiophene-2-carboxamide.

11. A compound according to claim 4 wherein the compound is 3-(1-methylethoxy)-5-methyl-N-1e,uns/H/ -tetrazol-5-yl-benzo[b]thiophene-2-carboxamide.

12. A compound according to claim 4 wherein the compound is 6-chloro-3-(1-me thylethoxy)-N-1e,uns/H/ -tetrazol-5-yl-benzo[b]thiophene-2-carboxamide.

13. A compound according to claim 4 wherein the compound is 3-methoxy-N-1e,uns/H/ -tetrazol-5-yl-benzo-[b]thiophene-2-carboxamide.

14. A compound according to claim 4 wherein the compound is 5-chloro-3-(1-methylethoxy)-N-1e,uns/H/ -tetrazole-5-yl-benzo[b]thiophene-2-carboxamide.

15. A compound according to claim 4 wherein the compound is 3-(1,1-dimethylethoxy)-5-methoxy-N-1e,uns/H/ -tetrazol-5-yl-benzo[b]thiophene -2-carboxamide.

16. A compound according to claim 4 wherein the compound is 3-(1-methylethoxy)-5-nitro-N-1e,uns/H/ -tetrazol-5-yl-be nzo[b]thiophene-2-carboxamide.

17. A compound according to claim 4 wherein the compound is 3,5-dimethoxy-N-1H-tetrazol-5-yl-benzo[b]thiophene-2-carboxamide.

18. A compound according to claim 4 wherein the compound is 6-methoxy-3-(1-methylethoxy)-N-1H-tetrazol-5-yl-benzo[b]thiophene-2-carboxamide.

19. A compound according to claim 4 wherein the compound is 3-(1-methylethoxy)-N-1H-tetrazol-5-yl-benzo[b]thiophene-2-carboxamide.

20. A compound according to claim 4 wherein the compound is 3-chloro-N-1H-tetrazol-5-yl-benzo[b]thiophene-2-carboxamide.

21. A compound according to claim 4 wherein the compound is 5-methoxy-3-[(1-methylethyl)thio]-N-1H-tetrazol-5-yl-benzothiophene-2-carboxamide.

22. A compound according to claim 4 wherein the compound is 3-[(1-methylethyl)thio]-N-1e,uns/H/ -tetrazol-5-yl-benzo[b]thiophene-2-carboxamide.

23. A compound according to claim 5 wherein the compound is 5-[5-methoxy-3-(1-methylethoxy)-benzo[b]thien-2-yl]-1e,uns/H/ -tetrazole.

24. A compound according to claim 5 wherein the compound is 5-[3-(1-methylethoxy)benzo[b]-thien-2-yl]-1e,uns/H/ -tetrazole.

25. A compound according to claim 3 wherein $R^3$ is A as defined in claim 1.

26. A compound according to claim 3 wherein $R^3$ is B as defined in claim 1.

27. A compound according to claim 25 wherein the compound is 3-methoxy-5-phenyl-N-1H-tetrazol-5-yl-2-benzofurancarboxamide.

28. A compound according to claim 25 wherein the compound is 3-ethoxy-5-phenyl-N-1H-tetrazol-5-yl-2-benzofurancarboxamide.

29. A compound according to claim 25 wherein the compound is 3-(1-methylethoxy)-5-phenyl-N-1H-tetrazol-5-yl-2-benzofurancarboxamide.

30. A compound according to claim 25 wherein the compound is 3-methoxy-7-phenyl-N-1H-tetrazol-5-yl-2-benzofurancarboxamide.

31. A compound according to claim 25 wherein the compound is 3-ethoxy-7-phenyl-N-1H-tetrazol-5-yl-2-benzofurancarboxamide.

32. A compound according to claim 25 wherein the compound is 3-(1-methylethoxy)-7-phenyl-N-1H-tetrazol-5-yl-2-benzofurancarboxamide.

33. A compound according to claim 25 wherein the compound is 3,6-dimethoxy-N-1H-tetrazol-5-yl-2-benzofurancarboxamide.

34. A compound according to claim 25 wherein the compound is 3,5-dimethoxy-N-1e,uns/H/ -tetrazol-5-yl-2-benzofurancarboxamide.

35. A compound according to claim 25 wherein the compound is 6-methoxy-3-phenylmethoxy-N-1e,uns/H/ -tetrazol-5-yl-2-benzofurancarboramide.

36. A compound according to claim 25 wherein the compound is 3,7-dimethoxy-N-1e,uns/H/ -tetrazol-5-yl-2-benzofurancarboxamide.

37. A compound according to claim 25 wherein the compound is 3-nonyloxy-7-methoxy-N-1e,uns/H/ -tetrazol-5-yl-2-benzofurancarboxamide.

38. A compound according to claim 25 wherein the compound is 3-acetylamino-N-1e,uns/H/ -tetrazol-5-yl-2-benzofurancarboxamide.

39. A compound according to claim 25 wherein the compound is 3-methoxy-N-(1e,uns/H/ -tetrazol-5-yl)-naphtho[2,3-b]furan-2-carboxamide.

40. A compound according to claim 25 wherein the compound is 5-methoxy-3-(1-methylethoxy-N-1H-tetrazol-5-yl-2-benzofurancarboxamide.

41. A compound according to claim 25 wherein the compound is 5-methoxy-3-phenylmethoxy-N-1H-tetrazol-5-yl-2-benzofurancarboxamide.

42. A compound according to claim 25 wherein the compound is 6-methoxy-3-(1-methylethoxy)-N-1H-tetrazol-5-yl-2-benzofurancarboxamide.

43. A compound according to claim 25 wherein the compound is 7-methoxy-3-(1-methylethoxy)-N-1H-tetrazol-5-yl-2-benzofurancarboxamide.

44. A compound according to claim 25 wherein the compound is 3-amino-N-1H-tetrazol-5-yl-2-benzofurancarboxamide.

45. A compound according to claim 26 wherein the compound is 5-(3-amino-2-benzofuranyl)-1H-tetrazole.

46. A compound according to claim 26 wherein the compound is 5-(3,6-dimethoxy-2-benzofuranyl)-1e,uns/H/ -tetrazole.

47. A compound according to claim 26 wherein the compound is 5-(3,5-dimethoxy-2-benzofuranyl)-1H-tetrazole.

48. A compound according to claim 26 wherein the compound is 5-(3,7-dimethoxy-2-benzofuranyl)-1H-tetrazole.

49. A compound according to claim 26 wherein the compound is 5-(3-acetylamino-2-benzofuranyl)-1H-tetrazole.

50. A pharmaceutical composition comprising an effective amount of a compound according to claim 1 in admixture with a pharmaceutically acceptable carrier.

51. A method of treating allergies in mammals which comprises administering to such mammal in need thereof an effective amount of a pharmaceutical compound according to claim 1.

* * * * *

UNITED STATES PATENT AND TRADEMARK OFFICE
CERTIFICATE OF CORRECTION

PATENT NO. : 4,703,053

DATED : October 27, 1987

INVENTOR(S) : David T. Connor, et al.

It is certified that error appears in the above—identified patent and that said Letters Patent is hereby corrected as shown below:

In Column 34, Line 11, change "5-methoxy-3-(1-methylethoxy-N-1H-tet-" to --5-methoxy-3-(1-methylethoxy)-N-1H-tet---.

Signed and Sealed this

Twenty-sixth Day of April, 1988

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO. : 4,703,053
DATED : October 27, 1987
INVENTOR(S) : David T. Connor, et al.

It is certified that error appears in the above—identified patent and that said Letters Patent is hereby corrected as shown below:

Column 32, Line 27, change "1e,uns/H/ " to --1$\underline{H}$--.

Column 32, Line 31, change "1e,uns/H/ " to --1$\underline{H}$--.

Column 32, Line 35, change "1e,uns/H/ " to --1$\underline{H}$--.

Column 32, Line 39, change "1e,uns/H/ " to --1$\underline{H}$--.

Column 32, Line 42, change "1e,uns/H/ " to --1$\underline{H}$--.

Column 32, Line 45, change "1e,uns/H/ " to --1$\underline{H}$--.

Column 32, Line 49, change "1e,uns/H/ " to --1$\underline{H}$--.

Column 32, Line 52, change "1e,uns/H/ " to --1$\underline{H}$--.

Column 33, Line 2, change "1e,uns/H/ " to --1$\underline{H}$--.

Column 33, Line 6, change "1e,uns/H/ " to --1$\underline{H}$--.

Column 33, Line 9, change "1e,uns/H/ " to --1$\underline{H}$--.

Column 33, Line 38, change "1e,uns/H/ " to --1$\underline{H}$--.

Column 33, Line 43, change "1e,uns/H/ " to --1$\underline{H}$--.

Column 33, Line 45, change "1e,uns/H/ " to --1H--.

Column 34, Line 2, change "1e,uns/H/ " to --1$\underline{H}$--.

Column 34, Line 5, change "1e,uns/H/ " to --1$\underline{H}$--.

UNITED STATES PATENT AND TRADEMARK OFFICE
CERTIFICATE OF CORRECTION

PATENT NO. : 4,703,053

DATED : October 27, 1987

INVENTOR(S) : David T. Connor, et al

It is certified that error appears in the above-identified patent and that said Letters Patent is hereby corrected as shown below:

Column 34, Line 8, change "1e,uns/H/" to --1$\underline{H}$ --.

Column 34, Line 29, change "1e,uns/H/" to --1$\underline{H}$ --.

Signed and Sealed this

Seventh Day of June, 1988

*Attest:*

DONALD J. QUIGG

*Attesting Officer*       *Commissioner of Patents and Trademarks*